US005871726A

United States Patent [19]
Henderson et al.

[11] Patent Number: 5,871,726
[45] Date of Patent: *Feb. 16, 1999

[54] TISSUE SPECIFIC AND TUMOR GROWTH SUPPERSSION BY ADENOVIRUS COMPRISING PROSTATE SPECIFIC ANTIGEN

[75] Inventors: Daniel Robert Henderson, Palo Alto; Eric Rodolph Schuur, Cupertino, both of Calif.

[73] Assignee: Calydon, Inc., Sunnyvale, Calif.

[*] Notice: The term of this patent shall not extend beyond the expiration date of Pat. No. 5,698,443.

[21] Appl. No.: 669,753

[22] Filed: Jun. 26, 1996

Related U.S. Application Data

[63] Continuation-in-part of Ser. No. 495,034, Jun. 27, 1995, Pat. No. 5,698,443.
[51] Int. Cl.$^6$ ............................. A61K 48/00; C12N 5/00; C12N 15/00
[52] U.S. Cl. .................... 424/93.2; 424/93.6; 435/320.1; 435/325; 435/456
[58] Field of Search ....................... 424/93.1; 435/240.1, 435/252.3; 514/44; 536/23.1

[56] References Cited

FOREIGN PATENT DOCUMENTS

| 94/28152 | 12/1994 | WIPO . |
|---|---|---|
| WO 95/11984 | 5/1995 | WIPO . |
| WO 96/10838 | 4/1996 | WIPO . |
| WO 96/16676 | 6/1996 | WIPO . |
| WO 96/17053 | 6/1996 | WIPO . |
| WO 96/34969 | 11/1996 | WIPO . |
| WO 96/36365 | 11/1996 | WIPO . |

OTHER PUBLICATIONS

An et al., "Expression of bacterial β–galactosidase in animal cells" *Mol. Cell. Biol.* (1982) 2:1628–1632.
Bailey et al., "Enteric adenovirus type 40: Expression of E1B Proteins in vitro and in vivo" *Virol.* (1993) 193:631–641.
Bailey et al. "Cell type specific regulation of expression from the Ad40 E1B promoter in recombinant Ad5/Ad40 viruses" *Virol.* (1994) 202:695–706.
Bridge et al., Redundant control of adenovirus late gene expression by early region 4 *J. Virol.* (1989) 63:631–638.
Calabresi et al., "Antineoplastic agents" *Goodman and Gilman's: The Pharmaceutical Basos of Therapeutics*, Permagon Press, New York (1990),pp. 1209–1263.
Chang et al., "Cancer gene therapy using novel tumor specific replication competent adenoviral vectors" *Cold Spring Harbor Gene Therapy Meeting* (Sep. 1996) p. 53 (abstract).
Dix et al., "Regulated splicing of adenovirus type 5 E4 transcripts and regulated cytoplasmic accumulation of E4 mRNA" *J. Virol.* (1993) 67:3226–3231.
Flint et al., "Regulation of adenovirus mRNA formation" *Adv. Virus Res.* (1986) 31:169–228.

Flint, "Expression of adenoviral genetic information in productively infected cells" *Biochim. Biophys. Acta* (1982) 651:175–208.
Graham et al., "Characteristics of a human cell line transformed by DNA from human adenovirus type 5" *J. Gen. Virol.* (1977) 36:59–72.
Graham, "Growth of 293 cells in suspension culture" *J. Gen. Virol.* (1987) 68:937–940.
Grand et al., "The structure and functions of the adenovirus early region 1 proteins" (1987) *Bio chem. J.* (1987) 241:25–38.
Griffith et al., "High affinity sodium–dependent nucleobase transport in cultured renal epithelial cells (LLC–PK$_1$)" *J. Biol. Chem.* (1993) 268:20085–20090.
Hayashi et al., "Expression of a thyroid hormone–responsive recombinant gene introduced into adult mice livers by replication–defective adenovirus can be regulated by endogenous thyroid hormone receptor" *J. Biol. Chem.* (1994) 269:23872–23875.
Helin et al., Heterodimerization of the transcriptional factors E2F–1 and DP–1 is required for binding to the adenovirus E4 (ORF6/7) protein *J. Virol.* (1994) 68:5027–5035.
Hirschowitz et al., "In vivo adenovirus–mediated gene transfer of the *Escherichia coli* cytosine deaminase gene to human colon carcinoma–derived tumors induces chemosensitivity to 5–Fluorocytosine" *Human Gene Therapy* (1995) 6:1055–1063.
Jaffe et al., "Adenovirus–mediated in vivo gene transfer and expression in normal rat liver" *Nature Genetics* (1992) 1:372–378.
Klessig et al., "Mutations that allow human Ad2 and Ad5 to express late genes in monkey cells map in the viral gene encoding the 72K DNA binding protein" *Cell* (1979) 17:957–966.
Ko et al., "Gene therapy for the treatment of androgen independent and prostate specific antigen producing human prostate cancer" *Cell. Biochem.* (1995) Supplement 21A, p. 423, abstract No. C6–529.
Kruijer et al., "Structure and organization of the gene coding for the DNA binding protein of adenovirus type 5" *Nucl. Acids Res.* (1981) 9:4439–4457.
Le Gal La Salle et al., "An adenovirus vector for gene transfer into neurons and glia in the brain" *Science* (1993) 259:988–990.
Lewis et al., "Isolation of two plaque variants from the adenovirus type 2–simian virus 40 hybrid population which differ in their efficiency in yielding simian virus 40" *J. Virol.* (1970) 5:413–420.

(List continued on next page.)

*Primary Examiner*—Deborah Crouch

[57] ABSTRACT

Host cell specific adenovirus vehicles are provided for transfecting target host cells. By providing for transcriptional initiating regulation dependent upon transcription factors that are only active in specific, limited cell types, virus replication will be restricted to the target cells. The modified adenovirus may be used as a vehicle for introducing new genetic capability, particularly associated with cytotoxicity for treating neoplasia.

32 Claims, 1 Drawing Sheet

OTHER PUBLICATIONS

Lewis et al., "Studies of nondefective adenovirus 2–simian virus 40 hybrid viruses" *J. Virol.* (1973) 11:655–664.

Mastrangeli et al., "Diversity of airway epithelial cell targets for in vivo recombinant adenovirus–mediated gene transfer" *J. Clin. Invest.* (1993) 91:225–234.

McKinnon et al., "Tn5 mutagenesis of the transforming genes of human adenovirus type 5" *Gene* (1982) 19:33–42.

Moolten et al., "Curability of tumors bearing herpes thymidine kinase genes transferred by retroviral vectors" *J. Natl. Cancer Inst.* (1990) 82:297–300.

Nevins, "Mechanisms of viral–mediated trans–activation of transcription" *Adv. Viral Res.* (1989) 37:35–83.

Quantin et al., "Adenovirus as an expression vector in muscle cells in vivo" *Proc. Natl. Acad. Sci. USA* (1992) 89:2581–2584.

Ragot et al., "Efficient adenovirus–mediated transfer of a human minidystrophin gene to skeletal muscle of mdx mice" *Nature* (1993) 361:647–650.

Rosenfeld et al., "Adenovirus–mediated transfer of a recombinant $\alpha 1$–antitripsin gene to the lung epithelium in vivo" *Science* (1991) 252;431–434.

Rosenfeld et al., "In vivo transfer of the human cystic fibrosis transmembrane conductance regulator gene to the airway epithelium" *Cell* (1992) 68:143–155.

Ross et al., "Defective synthesis of early region 4 mRNAs during abortive adenovirus infections in monkey cells" *J. Virol.* (1992) 66:3110–3117.

Stratford–Perricaudet et al., "Widespread long–term gene transfer to mouse skeletal muscle and heart" *J. Clin. Invest.* (1992) 90:626–630.

Stratford–Perricaudet et al., "Evaluation of the transfer and expression in mice of an enzyme–encoding gene using a human adenovirus vector" *Human Gene Therapy* (1990) 1:241–256.

Swaminathan et al., "Regulation of adenovirus E2 transpost unit" *Current Topics in 199/III Microbiology and Immunology* Capron et al., eds., (1995) pp. 177–194.

Taneja et al., "In vitro target specific gene therapy for prostate cancer utilizing a prostate specific antigen promoter–driven adenoviral vector" *Proc. Am. Assoc. Cancer Res.* (1994) 35:375 (abstract 2236).

Tijan et al., "Biological activity of purified simian virus 40 T antigen proteins" *Proc. Natl. Acad. Sci. USA* (1978) 75:1279–1283.

Virtanen et al., "mRNAs from human adenovirus 2 early region 4" *J. Virol.* (1984) 51:822–831.

Wang et al., "Expression of the APRT gene in an adenovirus vector system as a model for studying gene therapy" *Purine and Pyrimidine Metabolism in Man VII,* Part B, (1991) Harkness et al., eds., Plenum Press, New York, pp. 61–66.

Weinberg et al., "A cell line that supports the growth of a defective early region 4 deletion mutant of human adenovirus type 2" *Proc. Natl. Acad. Sci. USA* (1983) 80:5383–5386.

Zain et al., "Characterization and sequence analysis of a recombinant site in the hybrid virus Ad2$^+$ND$_1$" *J. Mol. Biol.* (1978) 120:13–31.

Gotoh, A., et al., "New Strategy of Toxic Gene Therapy for Human Prostate Cancer Cells," *Proceedings of the American Urological Association,* 153(April Suppl.):308A (1995).

Taneja, S.S., et al., "In vitro Target Specific Gene Therapy for Prostate Cancer Utilizing a Prostate Specific Antigen Promoter–Driven Adenoviral Vector," *Proceedings of the American Association for Cancer Research,* 35(0):375 (1994).

Ko, A.S.C., et al., "Gene Therapy for the Treatment of Androgen Indpedent and Prostate Specific Antigen Producing Human Prostate Cancer," *J. Cell. Biochem.,* Supp. 0, (21A):423 (1995).

Marshall, E., "Gene Therapy's Growing Pains," *Science,* 269:1050–1055 (1995).

Hodgson, C., "Advances in Vector Systems for Gene Therapy," *Exp. Opin. Ther. Patents,* 5(5):459–468 (1995).

Culver, K.W., et al., "Gene Therapy for Cancer," *TIG,* 10(5):174–178 (1994).

Miller, N., et al., "Targeted Vectors for Gene Therapy," *FASEB Journal,* 9:190–199 (1995).

Bett, A.J., et al., "Packing Capacity and Stability of Human Andenovirus Type 5 Vectors," *J. Of Virology,* 67(10):5911–5921 (1993).

Graham, F.L., "Covalently Closed Circles of Human Adenovirus DNA are Infectious," *The EMBO Journal,* 3(12):2917–2922 (1984).

Graham, F.L. and A.J. Van Der Eb, "A New Technique for the Assay of Infectivity of Human Adenovirus 5 DNA," *Virology,* 52:456–467 (1973).

Berkner, K.L. and P.A. Sharp, "Generation of Adenovirus by Transfection of Plasmids," *Nucleic Acids Research,* 11(17):6003–6020 (1983).

Takiff, H.E., et al., "Propagation and in vitro Studies of Previously Non–Cultivable Enteral Adenoviruses in 293 Cells," *The Lancet,* 832–834 (1981).

Bett, A.J., et al., "An Efficient and Flexible System for Contruction of Adenovirus Vectors with Insertions or Deletion in Early Regions 1 and 3," *PNAS, USA* 91:8802–8806 (1994).

Neve, R.,L. Trends in NNeurosciences 16(7):251–253, Jul. 1993.

Marshal. Science 269:1050–1055, Aug. 1995.

Culver et al. Trends in Genetics 10(5):174–178, May 1994.

Hodgson. Exp. Opin. Ther. Patents 5(5):459–468, 1995.

Miller et al. FASEB 9:190–199, Feb. 1995.

Gotoh et al. J. Urology 153, 4 Supp., 308A, Apr. 1995.

Taneja et al. Proc. Amer. Assoc. Canc. Res.,35(0):375, Mar. 1994.

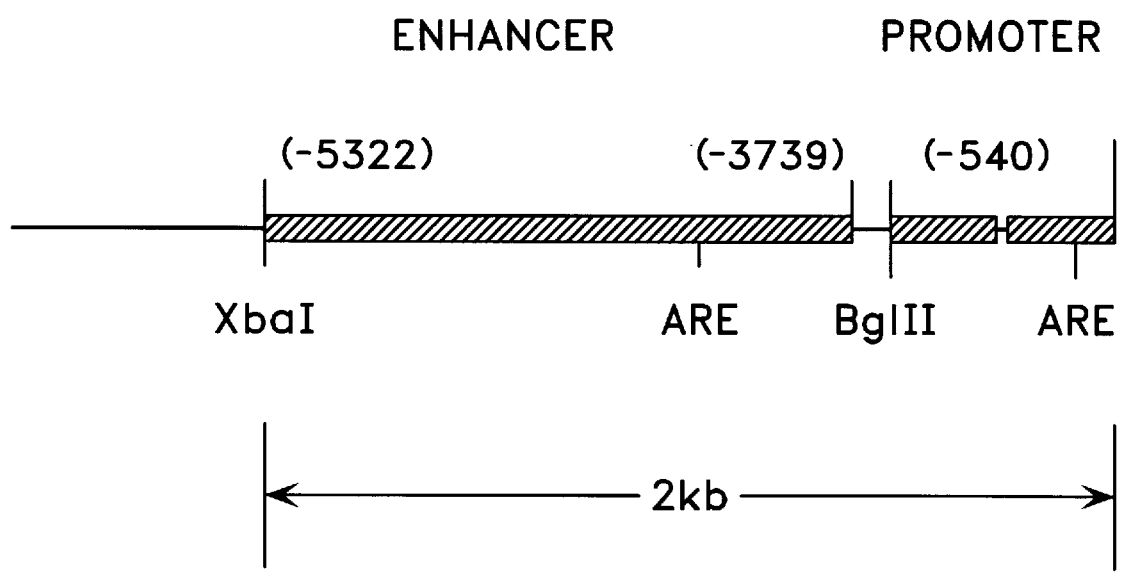

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:1:

GCGCAAGCTT GGGCTGGG                                                                            1 8

( 2 ) INFORMATION FOR SEQ ID NO:2:

( i ) SEQUENCE CHARACTERISTICS:
　　　　( A ) LENGTH: 22 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "Primer"

( x i ) SEQUENCE DESCRIPTION: SEQ ID NO:2:

GGAAGATCTA GAAATCTAGC TG                                            22

( 2 ) INFORMATION FOR SEQ ID NO:3:

( i ) SEQUENCE CHARACTERISTICS:
　　　　( A ) LENGTH: 33 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "Primer"

( x i ) SEQUENCE DESCRIPTION: SEQ ID NO:3:

GAATTCCTGC AGTCTAGACA TATGGGCGCC GAT                                33

( 2 ) INFORMATION FOR SEQ ID NO:4:

( i ) SEQUENCE CHARACTERISTICS:
　　　　( A ) LENGTH: 38 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "Primer"

( x i ) SEQUENCE DESCRIPTION: SEQ ID NO:4:

ATTGAATTCC TGCAGTTATG CGGTGACACG ATTTCCTG                           38

( 2 ) INFORMATION FOR SEQ ID NO:5:

( i ) SEQUENCE CHARACTERISTICS:
　　　　( A ) LENGTH: 25 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "Primer"

( x i ) SEQUENCE DESCRIPTION: SEQ ID NO:5:

GGACCTCGAG GTCTCCATGA GCTAC                                         25

( 2 ) INFORMATION FOR SEQ ID NO:6:

( i ) SEQUENCE CHARACTERISTICS:
　　　　( A ) LENGTH: 23 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "Primer"

( x i ) SEQUENCE DESCRIPTION: SEQ ID NO:6:

AGCTCGAGCT TCGGGATCCT GAG                                           23

( 2 ) INFORMATION FOR SEQ ID NO:7:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Primer"

( x i ) SEQUENCE DESCRIPTION: SEQ ID NO:7:

TCGTCTTCAA GAATTCTCA                                                                 19

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:8:

TTTCAGTCAC CGGTGTCGGA                                                                20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:9:

GCATTCTCTA GACACAGGTG                                                                20

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:10:

TCCGACACCG GGTGACCTGA AA                                                             22

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:11:

CATTAACCGG TACCTCTAGA AAATCTAGC                                                      29

( 2 ) INFORMATION FOR SEQ ID NO:12:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:12:

CATTAACCGG TAAGCTTGGG GCTGGGG 27

( 2 ) INFORMATION FOR SEQ ID NO:13:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:13:

CCGCTCGAGA TCACACTCCG CCACAC 26

( 2 ) INFORMATION FOR SEQ ID NO:14:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:14:

CCGCTCGAGC ACTCTTGAGT GCCA 24

( 2 ) INFORMATION FOR SEQ ID NO:15:

( i ) SEQUENCE CHARACTERISTICS:
( A ) LENGTH: 156 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:15:

TCGAGGGATG TTGTAGTAAA TTTGGGCGTA ACCGAGTAAG ATTTGGCCAT TTTCGCGGGA 60

AAACTGAATA AGACTCTTCG AAATCTGAAT AATTTTGTGT TACTCATAGC GCGTAATATT 120

TGTCTAGGGC CGCGGGGACT TTGACCGTTT ACGTGG 156

( 2 ) INFORMATION FOR SEQ ID NO:16:

( i ) SEQUENCE CHARACTERISTICS:
( A ) LENGTH: 156 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:16:

| | | | | | |
|---|---|---|---|---|---|
| GATCCCACGT | AAACGGTCAA | AGTCCCCGCG | GCCCTAGACA | AATATTACGC | GCTATGAGTA | 60
| ACACAAAATT | ATTCAGATTT | CGAAGAGTCT | TATTCAGTTT | TCCCGCGAAA | ATGGCCAAAT | 120
| CTTACTCGGT | TACGCCCAAA | TTTACTACAA | CATCC | | | 156

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:17:

GGAAGATCTG  AAATCTAGCT  GATATAG                                           27

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:18:

TTCTCGAGAA  GCTTGGGGCT  GGGG                                              24

( 2 ) INFORMATION FOR SEQ ID NO:19:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:19:

GTCGACGTGA  AATCTGAATA  ATTTTGTGTT  ACTCATAGC                             39

( 2 ) INFORMATION FOR SEQ ID NO:20:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:20:

CACCGGCGCA  CACCAAAAAC  GTC                                               23

( 2 ) INFORMATION FOR SEQ ID NO:21:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "Primer"

( x i ) SEQUENCE DESCRIPTION: SEQ ID NO:21:

TCGTCTTCAA GAATTCTCA 19

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:22:

GCCCACGGCC GCATTATATA C 21

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:23:

GTATATAATG CGGCCGTGGG C 21

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:24:

CCAGAAAATC CAGCAGGTAC C 21

( 2 ) INFORMATION FOR SEQ ID NO:25:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:25:

TAACGGCCGT CTAGAAATCT AGCTGA 26

( 2 ) INFORMATION FOR SEQ ID NO:26:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "Primer"

( x i ) SEQUENCE DESCRIPTION: SEQ ID NO:26:

TAACGGCCGA AGCTTGGGCT GGG 23

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:27:

TAACTCACGT TGTGCATTGT 20

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:28:

GGTGCCGTGC TCGAGTGGTG T 21

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:29:

ACACCACTCG AGCACGGCAC C 21

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:30:

GCTACTATTC GACAGTTTGT ACTG 24

( 2 ) INFORMATION FOR SEQ ID NO:31:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "Primer"

( x i ) SEQUENCE DESCRIPTION: SEQ ID NO:31:

GGACCTCGAG GTCTCCATGA GCTAC 25

( 2 ) INFORMATION FOR SEQ ID NO:32:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Primer"

( x i ) SEQUENCE DESCRIPTION: SEQ ID NO:32:

AGCTCGAGCT TCGGGATCCT GAG 23

( 2 ) INFORMATION FOR SEQ ID NO:33:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Primer"

( x i ) SEQUENCE DESCRIPTION: SEQ ID NO:33:

GGGTCGACGT ACCTCTAGAA ATCTAGC 27

( 2 ) INFORMATION FOR SEQ ID NO:34:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Primer"

( x i ) SEQUENCE DESCRIPTION: SEQ ID NO:34:

TTGTCGACAA GCTTGGGGCT GGGG 24

( 2 ) INFORMATION FOR SEQ ID NO:35:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Primer"

( x i ) SEQUENCE DESCRIPTION: SEQ ID NO:35:

GTTTGTGTAT TTTAGATCAA AGATGCTGCA 30

( 2 ) INFORMATION FOR SEQ ID NO:36:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: other nucleic acid -continued ( A ) DESCRIPTION: /desc = "Primer"

( x i ) SEQUENCE DESCRIPTION: SEQ ID NO:36:

GCATCTTTGA TCTAAAATAC ACAAAC 26

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:37:

TAAAGGAGGA GATCTGCCTA AAACACTGCA 30

( 2 ) INFORMATION FOR SEQ ID NO:38:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:38:

GTGTTTTAGG CAGATCTCCT CCTTT 25

( 2 ) INFORMATION FOR SEQ ID NO:39:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:39:

GCAACCCACC GGTGCTAATC AAGTATGGCA AAGGAGTAAG CGC 43

( 2 ) INFORMATION FOR SEQ ID NO:40:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:40:

TGGCCTTGCT AGACTGCTCC TTCAGC 26

TISSUE SPECIFIC AND TUMOR GROWTH SUPPERSSION BY ADENOVIRUS COMPRISING PROSTATE SPECIFIC ANTIGEN

CROSS REFERENCE TO RELATED APPLICATIONS

This application is a continuation-in-part of application Ser. No. 08/495,034, filed Jun. 27, 1995, now U.S. Pat. No. 5,698,443, the disclosure of which is herein incorporated by reference.

TECHNICAL FIELD

The field of this invention is cell transfection.

BACKGROUND

The ability to change the genotype and phenotype of cells in vitro and in vivo has many applications. For studying physiologic processes, particularly with dedicated cells, there is substantial interest in being able to modify the phenotype to affect a particular process. By enhancing or depressing the amount of a member of the physiological pathway, by inhibiting the activity of a member of the pathway, by providing an allele or mutated analog of the naturally occurring member, one may be able to unravel the role of the various members in the pathway, the order in which the members participate, the presence of alternative pathways and the like. Also, one can use the cells for producing proteins.

Adenovirus does not require cell proliferation for efficient transduction of cells. Adenovirus modified by introduction of a transgene provides for transient expression of proteins. Adenovirus can be rendered incompetent by inactivating one or more essential genes and then be packaged in a helper cell line for use in transfection. Thus, adenovirus affords a convenient vehicle for modifying cellular traits or killing cells, as appropriate.

For many medical applications, there is an interest in being able to specifically modify target cells in vivo or ex vivo. The modification can be associated with random DNA integration, whereby a genetic capability is introduced that complements a genetic defect intracellularly, provides for secretion of a product from the modified cells, which is otherwise indetectably produced or not produced by the host, provide protection from disease, particularly viral disease, and the like. In many situations, in order to be effective, one must have a high efficiency of transfection of the target cells. This is particularly true for in vivo modification. In addition, one would wish to have a high specificity for the target cells, as compared to other cells that may be present ex vivo or in vivo.

Gene therapy involves the transfer of cloned genes to target cells. A variety of viral and non-viral vehicles have been developed to transfer these genes. Of the viruses, retroviruses, herpes virus, adeno-associated virus, Sindbis virus, poxvirus and adenoviruses have been used for gene transfer. These vehicles all have different properties. For example, retroviruses transduce genes in vitro with high efficiency by integrating the transduced gene into the chromosome following division of infected cells. Adeno-associated viruses can stably integrate into and express transduced genes in both dividing and quiescent cells. In contrast, liposomes and adenovirus allow only transient gene expression, and transduce both dividing and quiescent target cells.

Of the viruses, adenoviruses are among the most easily produced and purified, whereas retroviruses are unstable, difficult to produce and impossible to purify. Both classes of virus transduce cells with high efficiency. Liposomes hold the promise of allowing repeat doses of genes for, unlike viruses, they are not immunogenetic. However, liposomes complexed with DNA are difficult to produce in commercial quantities, and are inefficient gene transfer vehicles, most often transducing fewer than one percent of target cells.

There are two major divisions of gene therapy protocols: in vivo and ex vivo. In vivo refers to administration of the therapeutic directly to the patient, usually by inhalation or injection, although oral administration has been suggested in some instances. Ex vivo gene therapy refers to the process of removing cells from a patient, for example in a biopsy, placing the cells into tissue culture, transferring genes to the cells in tissue culture, characterizing the newly genetically engineered cells, and finally returning the cells to the patient by intravenous infusion. Therapeutically, retroviruses are most often used for ex vivo transfer, whereas adenoviruses and liposomes are most often used for in vivo gene transfer.

In the treatment of cancer by replication defective adenoviruses, the host immune response limits the duration of repeat doses of the therapeutic at two levels. First, the adenovirus delivery vehicle itself is immunogenic. Second, late virus genes are frequently expressed in transduced cells, eliciting cellular immunity. Thus, the ability to repeatedly administer cytokines, tumor suppressor genes, ribozymes or suicide genes is limited by the transient nature of gene expression, and the immunogenicity of both the gene transfer vehicle and the viral gene products of the transfer vehicle.

The first case, the immunogenicity of the vector, is akin to the problem facing mouse monoclonal antibodies complexed with bacterial toxins that are directed against tumor-specific antigens. Use of these proteins as a therapeutic, popular a decade ago, failed due to the high doses required and ultimately, to immunogenicity. The same fate may befall replication defective adenoviruses, unless the efficacy can be improved to achieve clinical useful therapeutic endpoints before immunogenicity of a transfer vehicle limits repeat usage.

In the second case, steps have been taken to eliminate the unwanted transcription and expression of late adenovirus genes in transduced cells, with the resulting immunogenicity.

There is, therefore, substantial interest in being able to develop viral vectors which substantially reduce the present limitations and restrictions on the use of such vectors in vivo.

RELEVANT LITERATURE

Graham and Van de Eb (1973) Virology 52: 456–467; Takiff et al. (1981) Lancet ii: 832–834; Berkner and Sharp (1983) Nucleic Acid Research 11: 6003–6020; Graham (1984) EMBO J 3: 2917–2922; Bett et al. (1993) J. Virology 67: 5911–5921; and Bett et al. (1994) Proc. Natl. Acad. Sci. USA 91: 8802–8806 describe adenoviruses that have been genetically modified to produce replication defective gene transfer vehicles. In these vehicles, the early adenovirus gene products E1A and E1B are deleted and provided in trans by the packaging cell line 293 developed by Frank Graham (Graham et al. (1987) J. Gen. Birol. 36: 59–72 and Graham (1977) J. Genetic Virology 68: 937–940). The gene to be transduced is commonly inserted into adenovirus in the deleted E1A and E1B region of the virus genome Bett et al.

(1994), supra. Adenovirus vectors as vehicles for efficient transduction of genes have been described by Stratford-Perricaudet (1990) *Human Gene Therapy* 1: 241–256; Rosenfeld (1991) *Science* 252: 431–434; Wang et al. (1991) *Adv. Exp. Med. Biol.* 309: 61–66; Jaffe et al. (1992) *Nat. Gent.* 1: 372–378; Quantin et al. (1992) *Proc. Natl. Acad. Sci. USA* 89: 2581–2584; Rosenfeld et al. (1992) *Cell* 68: 143–155; Stratford-Perricaudet et al. (1992) *J. Clin. Invest.* 90: 626–630; Le Gal Le Salle et al. (1993) *Science* 259: 988–990; Mastrangeli et al. (1993) *J. Clin. Invest.* 91: 225–234; Ragot et al. (1993) *Nature* 361: 647–650; Hayaski et al. (1994) *J. Biol. Chem.* 269: 23872–23875.

SUMMARY OF THE INVENTION

Adenovirus vectors, and methods for their use as vehicles for the transduction of restricted cell types, are provided. The adenovirus vectors are either replication defective or competetent. For replication defective adenovirus vectors, the adenoviruses can only be propagated in target cells in which early genes can be complemented in trans. Additionally, one or more late genes and/or one or more transgenes may be under the control of a transcriptional initiation region that is transcriptionally active only in the target cells of interest. For replication competent adenovirus vectors, one or more of the promoters of the early and/or late genes essential for propagation is replaced with the transcriptional initiation region described above, where a transgene under a cell specific promoter may also be present.

The adenovirus vectors find use in the treatment of various indications and for making mammalian hosts that are transiently transgenic, and allowing for regulated adenovirus propagation and transgene expression, in parallel with the cellular regulation of the endogenous transcriptional initiation region. For the adenovirus which is transcriptionally competent in target cells, the adenovirus may be used to kill the cells, while optionally producing one or more proteins of interest.

BRIEF DESCRIPTION OF THE DRAWINGS

FIG. 1 is a schematic drawing depicting a PSE.

DESCRIPTION OF THE SPECIFIC EMBODIMENTS

Replication defective or replication competent adenovirus vehicles are provided. The viruses comprise at least one gene under the transcriptional control of a transcriptional initiation region specifically regulated by target host cells. The genes that are regulated by the specifically regulated transcriptional initiation region may be early or late adenovirus genes and/or transgenes. By providing for regulated transcription restricted to specific host cell targets, one can provide for adenoviruses that can be used as vehicles for introducing genetic capability into host target cells, as distinct from other host cell types. The transgenes serve to modify the genotype or phenotype of the target cell, in addition to any modification of the genotype or phenotype resulting from the presence of the adenovirus. With competent adenoviruses, proliferation of the adenovirus may be used for its cytotoxic effect.

There are a number of different types of adenovirus, such as Ad2, Ad5, and Ad40, which may differ to minor or significant degrees. Particularly, Ad5 and Ad40 differ as to their host cell tropism, as well as the nature of the disease induced by the virus. For the purpose of the subject invention, Ad5 will be exemplified.

The genes of the adenovirus that are of interest for the subject invention may be divided into two groups, the early genes and the late genes, the expression of the latter being controlled by the major late promoter. Of the early genes, there are E1A, E1B, E2, E3 and E4. The E1A gene is expressed immediately after viral infection (0–2 h) and before any other viral genes. E1A protein acts as a transacting positive-acting transcriptional regulatory factor, and is required for the expression of the other early viral genes and the promoter proximal major late genes. Despite the nomenclature, the promoter proximal genes driven by the major late promoter are expressed during early times after Ad5 infection. In the absence of a functional E1A gene, viral infection does not proceed, because the gene products necessary for viral DNA replication are not produced.

The E1B protein functions in trans and is necessary for transport of late mRNA from the nucleus to the cytoplasm. Defects in E1B expression result in poor expression of late viral proteins and an inability to shut off host cell protein synthesis.

The E4 gene has a number of transcription products. Open reading frames (ORF) 3 and ORF 6 of the E4 transcription unit increase the accumulation of major late transcription unit mRNAs by binding the 55-kDa protein from E1B and heterodimers of E2F-1 and DP-1. In the absence of functional protein from ORF3 and ORF6, plaques are produced with an efficiency less than $10^{-6}$ of that of wild type virus.

The major late genes relevant to the subject invention are genes such as L1, L2 and L3, which encode proteins of the AD5 virus virion.

Regions of the adenovirus which may be deleted, usually at least 500 nt, more usually at least about 1 knt, include in the AD5 genome nucleotides 300 to 3600 in E1, particularly 342 to 3523; 27000 to 31000, particularly 28133 to 30818 or 27865 to 30995 in E3. The deletion will be at least sufficient for insertion of the desired construct and allow for packaging.

The subject vectors can be used for a wide variety of purposes. The purpose will vary with the target cell. Suitable target cells are characterized by the transcriptional activation of the cell specific transcriptional response element in the adenovirus vehicle. The transcription initiation region will usually be activated in less than about 5%, more usually less than about 1%, and desirably by less than about 0.1% of the cells in the host.

Regulation of transcriptional activation is the result of interaction between transcriptional activators bound to cis-regulatory elements, factors bound to basal transcriptional elements and the activity of transcriptional mediators, or coactivators. The absence or presence of any of these factors may affect the level of transcription. Additionally, factors may be present in an inactive form, where the factors are activated through chemical modification, particularly as the result of a cellular signaling mechanism. In some cases, signaling molecules are able to act directly to activate transcription. Any of these mechanisms may operate to limit the types of cells in which the vehicle transcription initiation region is active.

It will understood by one of skill in the art that very low basal levels of transcription may be present in non-targeted cell types. By transcriptional activation, it is intended that trancription will be increased above basal levels in the target cell by at least about 100 fold, more usually by at least about 1000 fold.

The cell specific response element may be used with an adenovirus gene that is essential for propagation, so that replication competence is only achievable in the target cell, and/or with a transgene for changing the phenotype of the target cell. By transgene is intended any gene that is not present in wild-type adenovirus, frequently the transgene will also not be expressed in the target cell, prior to introduction by the adenovirus.

As exemplified by employing a cell specific response element comprising a promoter and enhancer construct specific for prostate cells, various genetic capabilities may be introduced into prostate cells expressing prostate specific antigen. Of particular interest is the opportunity to introduce cytotoxic effects that are controlled by a transcriptional initiation region specifically active in prostate cells. Other cell types that have specific active transcription factors associated with a state for which modulation is desirable include leukocytes, particularly lymphocytes, epithelial cells, endothelial cells, hepatic cells, pancreatic cells, neuronal cells, and keratinocytes. Since the adenovirus results in transient expression (approximately 6 to 8 weeks), one can provide transient capability to cells, where the desired result only requires a limited period for response.

Purposes for introducing transient expression include indications that may be treated involving undesired proliferation other than tumors, such as psoriatic lesions, restenosis, wound healing, tissue repair, enhanced immune response, resistance to infection, production of factors, enhanced proliferation, investigation of metabolic or other physiological pathways, comparison of activity of cells in the presence and absence of the adenovirus introduced transgene, by comparing the activity of the cell before, during and after the modification with the adenovirus, etc. The subject vectors can be used to free a mixture of cells of a particular group of cells, where the group of cells is the target cells. By having the adenovirus be selectively competent for propagation in the target cells, only those cells will be killed on proliferation of the adenovirus. By combining the adenovirus with the mixture of cells, for example, in culture or in vivo, the adenovirus will only be capable of proliferation in the target cells. In this way cells other than the target cells will not be affected by the adenovirus, while the target cells will be killed. The expansion of the adenovirus due to propagation in the target cells will ensure that the mixture is substantially freed of the target cells. Once the target cells are destroyed, the adenovirus will no longer be capable of propagation, but in culture may be retained so as to continually monitor the mixture for recurrence of the target cell, e.g. a mutated cell or neoplastic cell.

By identifying genes that are expressed specifically by the target host cells, based on the nature of the cells, their level of maturity or their condition, the target cell specific response element can be used to provide genetic capability to such cells, where the genetic capability will be absent in other cells, even when transfected with the adenovirus vehicle.

Depending upon the target cell, various enhancers may be used to provide for target cell specific transcription. With lymphocytes, for B cells one may use the Ig enhancer, for T cells one may use the T cell receptor promoter. For the different muscle cells, one may use the promoters for the different myosins. For endothelial cells, one may use the different promoters for the different selecting. For each type of cell, there will be specific proteins associated with the cell, which allows for target cell specific transcription.

The region that is employed to provide cell specificity dependent upon androgens, particularly in prostate cells, involves an approximately 1.5 kb enhancer region and a 0.5 kb promoter region. The enhancer region in humans is located between nt −5322 and nt −3739, relative to the transcription start site of the prostate specific antigen (PSA) gene. The promoter consists of nt −540 to nt +8. Juxtaposition of the two genetic elements yields a fully functional, minimal prostate-specific enhancer promoter (PSE). The enhancer contains three regions that bind prostate-specific DNA binding proteins, one of which contains a putative androgen response element. The promoter region contains typical TATA and CAAT boxes as well as a second putative androgen response element.

The vectors are conveniently prepared by employing two plasmids, one plasmid providing for the left hand region of adenovirus and the other plasmid providing for the right hand region, where the two plasmids share at least about 500 nt of middle region for homologous recombination. In this way, each plasmid, as desired, may be independently manipulated, followed by cotransfection in a competent host, providing complementing genes as appropriate, or the appropriate transcription factors for initiation of transcription from the PSE for propagation of the adenovirus.

For convenience, plasmids are available that provide the necessary portions of the adenovirus. Plasmid pXC.1 (McKinnon (1982) Gene 19: 33–42) contains the wild-type left-hand end of Ad5. pBHG10 provides the right-hand end of Ad5, with a deletion in E3. The deletion in E3 provides room in the virus to insert the 2 kb minimal PSE without deleting the wild-type enhancer-promoter. The gene for E3 is located on the opposite strand from E4 (r-strand).

For manipulation of the early genes, the transcription start site of Ad5 E1A is at nt 560 and the ATG start site of the E1A protein is at nt 610 in the virus genome. This region can be used for insertion of the cell specific element, e.g. PSE. Conveniently, a restriction site may be introduced by employing the polymerase chain reaction (PCR), where the primer that is employed may be limited to the Ad5 genome, or may involve a portion of the plasmid carrying the Ad5 genomic DNA. For example, where pBR322 is the backbone, the primers may use the EcoRI site in the pBR322 backbone and the Xpa1 site at nt 1339 of Ad5. By carrying out the PCR in two steps, where overlapping primers at the center of the region introduce a sequence change resulting in a unique restriction site, one can provide for insertion of the cell specific response element at that site.

A similar strategy may also be used for insertion of the cell specific response element to regulate E1B. The E1B promoter of Ad5 consists of a single high-affinity recognition site for Sp1 and a TATA box. This region extends from 1636 to _1701 nt. By insertion of the cell specific response element in this region, one can provide for cell specific transcription of the E1B gene. By employing the left-hand region modified with the cell specific response element regulating E1A, as the template for introducing the cell specific response element to regulate E1B, the resulting adenovirus will be dependent upon the cell specific transcription factors for expression of both E1A and E1B.

For E4, one must use the right hand portion of the adenovirus genome. The E4 transcription start site is predominantly at nt 35605, the TATA box at nt 35631 and the first AUG/CUG of ORF1 is at nt 35532 (Virtanen et al. (1984) J. Virol. 51: 822–831). Using any of the above strategies for the other genes, the cell specific response element may be introduced in the region between the transcription start site and the initiation codon. Once again, by employing a previously manipulated adenovirus genome, one can provide for a plurality of genes being dependent upon the target cell specific transcription factor, insuring that the adenovirus will be incapable of replication in cells lacking these transcription factors.

For replication defective viruses, one need only inactivate one or more of the genes essential for replication, carrying out the modifications of the genome in appropriate host cells which can complement the defect, so as to provide propagation of the replication defective viruses. The host cells may then be used to package the virus for transduction of target cells.

Use of competent adenovirus, which is competent in particular target cells, allow for proliferation of the adenovirus in the target cells resulting in the death of the host cells and proliferation of the adenovirus to other host cells. To further ensure cytotoxicity, one may have one or more transgenes present which have cytotoxic effect. In this way one can provide high confidence that the target cells will be destroyed while providing for the appropriate level of expression of the cytotoxic agents).

Genetic capability that may be introduced into the adenovirus vehicle includes a factor capable of initiating apoptosis, antisense or ribozymes, which among other capabilities may be directed to mRNAs encoding proteins essential for proliferation, such as structural proteins, transcription factors, polymerases, etc., viral or other pathogenic proteins, where the pathogen proliferates intracellularly, cytotoxic proteins, e.g. the a chains of diphtheria, ricin, abrin, etc., genes that encode an engineered cytoplasmic variant of a nuclease (e.g. RNase A) or protease (e.g. trypsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFN-α, -β, -γ, TNF-α, -β, TGF-α, -β, NGF, and the like.

Other opportunities for specific genetic modification include T cells, such as tumor infiltrating lymphocytes (TILs), where the TILs may be modified to enhance expansion, enhance cytotoxicity, reduce response to proliferation inhibitors, enhance expression of lymphokines, etc. One may also wish to enhance target cell vulnerability by providing for expression of specific surface membrane proteins, e.g. B7, SV40 T antigen mutants, etc.

The modified viruses may be delivered to the target cell in a variety of ways, depending upon whether the cells are in culture, ex vivo or in vivo. For the prostate, for the most part, the cells will be delivered in vivo. Delivery can be achieved in a variety of ways, employing liposomes, direct injection, catheters, intravenpis inhalation, topical applications, etc. Due to the high efficiency of transfection of adenoviruses, one can achieve a high level of modified cells. In the case of neoplasia, where toxins are produced, the toxins will be released locally, so as to affect cells which may not have been successfully transfected. In this manner, one can specifically eliminate the neoplastic cells, without significant effect on the normal cells. In addition, expression of adenovirus proteins will serve to activate the immune system against the target cells. Finally, proliferation of the adenovirus in a host cell will lead to cell death.

The adenovirus may be administered in an appropriate physiologically acceptable carrier at a dose of about $10^4$ to $\_10^{11}$. The multiplicity of infection will generally be in the range of about 0.001 to 100. The viruses may be administered one or more times, depending upon the immune response potential of the host. If necessary, the immune response may be diminished by employing a variety of immunosuppressants, so as to permit repetitive administration, without a strong immune response.

The following examples are offered by way of illustration and not by way of limitation.

EXPERIMENTAL

I. Replication Defective Adenoviruses with Insertions in ΔE1 and ΔE3

The PSE enhancer region is located between nt −5322 and nt −3739 relative to the transcription start site of the prostate specific antigen gene. The promoter consists of nt −540 to nt +8. Juxtaposition of these two genetic elements yields to a fully functional minimal PSE.

A diagram of the PSE used is shown in FIG. 1. Shuttle vectors for the construction of recombinant adenovirus vectors which are replication defective can be constructed by deleting most or all of the E1 region of the Adenovirus genome and inserting restriction sites for the insertion of foreign DNA. One such vector system has been described by F. Graham and co-workers (Graham (1984) *EMBO. J*, 3: 2917–2922; Graham (1987) *J. Gen. Virol.* 68: 937–940; Graham and Smiley (1977) ibid 36: 59–72 and Graham and Van der Eb (1973) *Virology* 52: 456–467. In this system, the plasmids ΔE1sp1A and ΔE1sp1B contain the leftmost portion of the Ad5 genome except for sequences deleted between Ad5 nt 342 and 3523. In the place of the deletion is a multiple cloning site which is in opposite orientation in the two plasmids. An alternative location for the insertion of foreign DNA is in the E3 region of the plasmids BHG10 and BHG11 (Bett (1994) *PNAS* 91: 8802–8806) at a PacI cloning site which replaces the Ad5 E3 sequences 28133 to 30818 and 27865 to 30995, respectively. Removal of the E1 and/or E3 sequences provides room for the insertion of the PSE coupled to a reporter or effector gene.

A. PSE Driving Gene Expression in ΔE1.

1. PSE-CAT in ΔE1. The PSE driving the reporter CAT gene was inserted in the E1 deletion of ΔE1sp1A and ΔE1sp1B as follows. The XbaI/BamHI fragment of pCAT basic (Promega) containing the CAT gene coding sequences followed by the SV40 polyadenylation signal sequences was ligated to similarly cut ΔE1sp1A or ΔE1sp1B to yield CN83 and CN112, respectively. The HinDIII site between the PSE and PSA promoter of CN65 (Schuur et al. (1996) *J. Biol. Chem.* 271: 7043–7051) was removed by partial digestion with HinDIII, followed by endfilling with Klenow and relegation to generate CN84. The PSE PCR product for insertion into CN83 and CN112 was prepared by amplification of CN84 with primers:

18.69.1, 5'-GCGCAAGCTTGGGCTGGG, [SEQ ID NO: 01]

containing a HinDIII site, and 18.69.2, 5'-GGAAGATCTAGAAATCTAGCTG, [SEQ ID NO: 02]

containing BglII and XbaI sites. This DNA fragment was cleaved with BglII and HinDIII, then ligated to similarly cut CN83 and CN112 to generate plasmids CN99 and CN117, respectively. In CN99 the PSE-CAT transcription unit is in the left to right orientation relative to the Ad5 1-strand, while in CN117 the PSE-CAT unit is in the right to left orientation. The viruses derived by homologous recombination were designated CN710 (plasmids CN117 and BHG11), and CN714 (plasmids CN99 and BHG10 {McKinnon, et al., (1982) *Gene* 19: 33–42}).

2. PSE-β-galactosidase in ΔE1. Viral plasmids in which the PSE-β-galactosidase transcription unit was inserted in the E1 deletion of ΔE1sp1A and ΔE1sp1B were also constructed using a similar strategy to that used to construct the PSE-CAT virus plasmids. The XbaI fragment of pCMVbeta (Clonetech) containing the β-galactosidase gene flanked by the SV40 small t intron at the 5' end and the SV40 polyadenlylation signal sequences at the 3' end was inserted in the XbaI cut ΔE1sp1A and sp1B plasmids to construct CN85 and CN86, respectively. The PSE was amplified from CN84 as described for the PSE-CAT plasmids and ligated into BglII/HinDIII cut CN85 and CN86 to construct CN93 and CN138, respectively. In CN93 the PSE-b-galactosidase transcription unit is in the left to right orientation relative to the Ad5 1-strand, while in CN138 the PSE-β-galactosidase unit is in the right to left orientation. The viruses derived by homologous recombination were CN715 (from plasmids CN138 and BHG10), CN700 (from plasmids CN92 and BHG10), CN701 (from plasmids CN93 and BHG10), and CN709 (from plasmids CN116 and BHG11).

3. PSE-Diphtheria A toxin gene in ΔE1. The reporter gene insertions represented test systems for the insertion of therapeutic genes in E1 under control of the PSE. The plasmid pCAT basic (Promega) was cleaved with BamHI, then a partial digest was performed with XhoII to cleave the SV40 polyadenylation sequences from the rest of the plasmid DNA. The 800 base pair SV40 fragment was isolated and cloned into the BamHI site of Bluescript KSII+ with the XhoII end closest to the EcoRI site in the Bluescript polylinker. This clone was designated CN10. The Diphtheria toxin gene A chain sequences were inserted in the E1 region under control of the PSE as follows. The A chain sequences from the diphtheria toxin gene were PCR amplified with primers containing required restriction sites and translation control sequences:

7.18.1, 5'-GAATTCCTGCAGTCTAGACATATGGGCGCCGAT, [SEQ ID NO: 03]

containing sites for EcoRI and PstI and an initiation codon.

7.18.2. 5'-ATTGAATTCCTGCAGTTATGCGGTGACACGATTTCCTG, [SEQ ID NO: 04]

containing sites for EcoRI, PstI, and a stop codon.

The PCR amplification product was cleaved with EcoRI and ligated to similarly cleaved CN10 to generate CN44 with the DTA sequences in the correct orientation relative to the SV40 sequences. The DTA plus SV40 sequences were inserted into ΔE1sp1A and ΔE1sp1B as XbaI/BamHI fragments to yield CN120 and CN82, respectively. The PSE was PCR amplified from CN84 and ligated into CN120 and CN82 as described for the CAT constructs to produce CN123 and CN98, respectively. In CN123 the PSE-DTA transcription unit is in the left to right orientation relative to the Ad5 1-strand, while in CN98 the PSE-DTA unit is in the right to left orientation. Homologous recombination of CN98 and BHG10 yielded the virus CN721; homologous recombination of CN123 and BHG10 yielded the virus CN722.

B. PSE Driving Gene Expression in ΔE3.

Insertion of PSE driven transcription units in E3 was tested by cloning the PSE-CAT transcription unit into the PacI site of BHG11. To prepare the transcription unit for insertion into BHG11 the KpnI/SacI fragment of CN105 was ligated to similarly cut pABS.4 to construct CN175 which adds a kanamycin gene for selection and PacI sites at each end. The PacI fragment of CN175 was then ligated to PacI cut BHG11 and clones with insertions in both orientations were identified: CN301 contains the PSE-CAT unit in the left to right orientation and CN302 contains the PSE-CAT unit in the right to left orientation. CN301 and CN302 were then cleaved with SwaI to excise the kanamycin gene fragment, then relegated to yield CN303 and CN304.

Virus Construction

A human embryonic kidney cell line, 293, efficiently expresses E1A and E1B genes of AD5 and exhibits a high transfection efficiency with adenovirus DNA. The 293 cells were co-transfected with one left end Ad5 plasmid and one right end Ad5 plasmid. Homologous recombination generates adenoviruses with the required genetic elements for replication in 293 cells which provide E1A and E1B proteins in trans to complement defects in synthesis of these proteins. For the construction of mutants in the E4 region, the co-transfection and homologous recombination were performed in W162 cells (Weinberg & Ketner (1983) *PNAS* 80: 5383–5386) which provide E4 proteins in trans to complement defects in synthesis of these proteins.

The plasmids to be combined are co-transfected into cells using cationic liposomes such as Lipofectin (DOTMA:DOPE, Life Technologies) by combining the two plasmids, then mixing the plasmid DNA solution (10 mg of each plasmid in 200 μl of minimum essential medium without serum or other additives) with a four fold molar excess of liposomes in 200 μl of the same buffer. The DNA-lipid complexes are then placed on the cells and incubated at 37° C., 5% $CO_2$ for 16 hours. After incubation the medium was changed to MEM with 10% fetal bovine serum and the cells are further incubated at 37° C., 5% $CO_2$ for two weeks with two changes of medium. At the end of this time the cells and medium were transferred to tubes, freeze-thawed three times, and the lysate was used to infect 293 (or W162) cells at the proper dilution to detect individual viruses as plaques.

Plaques obtained were plaque purified twice, and viruses were characterized for presence of desired sequences by PCR and occasionally by DNA sequencing. For further experimentation the viruses were prepared on a larger scale by cesium chloride gradient centrifugation.

The table below lists the combinations of right end and left end Ad5 plasmids used to generate recombinant Ad5 with the desired features:

| Virus | Name | Left End Plasmid | Right End Plasmid |
|---|---|---|---|
| PSE-CAT (+) | CN710 | CN117 | BHG11 |
| PSE-CAT (−) | CN714 | CN99 | BHG10 |
| PSE-βGal (+) | CN715 | CN138 | BHG10 |
| PSE-βGal (−) | CN700, 701, 709 | CN92, CN93, CN116 | BHG10/11 |
| PSE-DTA (+) | CN722 | CN123 | BHG10 |
| PSE-DTA (−) | CN721 | CN98 | BHG10 |
| PSE-CAT in E3 | | ΔE1sp1A | |

II. Replication Competent Prostate-Specific Attenuated Adenoviruses.

A. Ad5 with PSE Driving Expression of E1A

The cloning and characterization of a minimal prostate-specific enhancer (PSE) is described in Prostate Specific Antigen Expression is Regulated by an upstream Enhancer (Schuur et al., supra). Plasmid CN71 contains our minimal PSE (from −5322 bp to −3875 bp relative to the transcription start site of the PSA gene) and −532 to +11 of the PSA promoter. CN71 was cut with XhoI/HindIII which removes the PSA promoter. A shorter promoter, from −230 to +7, amplified by PCR using primers:

18.119, 5'-GGACCTCGAGGTCTCCATGAGCTAC, [SEQ ID NO: 05]
and
15.59B, 5'-AGCTCGAGCTTCGGGATCCTGAG [SEQ ID NO: 06].

The PCR product was cut with XhoI/HindIII and ligated back into XhoI/HindIII cut CN71 creating CN105.

1. Attenuated Ad5 with PSE Driving E1A and Retaining the Endogenous Ad5 E1A Promoter and Enhancer.

The E1A gene is expressed immediately after viral infection (0–2 hours) and before any other viral genes. The E1A protein acts as a trans-acting, positive-acting transcriptional regulatory factor required for the expression of the other early viral genes, E1B, E2, E3, E4, and the promoter proximal genes of the major late genes. Despite the nomenclature, the promoter proximal genes driven by the major late promoter are expressed during early times after Ad5 infection (Flint (1982) *Biochem. Biophys. Acta* 651: 175–208; Flint (1986) *Advances Virus Research* 31: 169–228; Grand (1987) *Biochem. J.* 241: 25–38). In the absence of a functional E1A gene, viral infection does not proceed for the gene products necessary for viral DNA replication are not produced (Nevins (1989) *Adv. Virus Res.* 31: 35–81). The transcription start site of Ad5 E1A is at nt 560 and the ATG start site of the E1A protein is at nt 610 in the virus genome.

pXC.1 was purchased from Microbix Biosystems Inc. Toronto). pXC.1 contains Adenovirus 5 sequences from bp22 to 5790. We have introduced an AgeI site 12 bp 5' to the E1A initiation codon (Ad5 nucleotide 547) by oligodirected mutagenesis and linked PCR. The plasmid pXC.1 was PCR amplified using primers:

15.133A, 5'-TCGTCTTCAAGAATTCTCA [SEQ ID NO: 07], containing an EcoRI site, and 15.134B, 5'-TTTCAGTCACCGGTGTCGGA [SEQ ID NO: 08], containing an extra A to introduce an AgeI site. This created a segment from the EcoRI site in the pBR322 backbone to Ad5 nt 560. A second segment of pXC.1 from Ad nucleotide 541 to the XbaI site at Ad nucleotide 1339 was amplified using primers:

15.133B, 5'-GCATTCTCTAGACACAGGTG [SEQ ID NO: 09]

containing an XbaI site, and 15.133A, 5'-TCCGACACCGGGTGACCTGAAA [SEQ ID NO: 10], containing an extra T to introduce an AgeI site. A mixture of these two PCR amplified DNA segments was mixed and amplified with primers 3 and 4 to create a DNA segment from the EcoRI site to the XbaI site of pXC.1. This DNA segment encompasses the leftmost 1317 bases of Adenovirus sequence and contained an AgeI site at Ad nucleotide 547. This DNA segment was used to replace the corresponding segment of pXC.1 to create CN95. Similarly, a PSE with Age1 ends was PCR amplified from CN105 using primers:

15.176A, 5'-CATTAACCGGTACCTCTAGAAAATCTAGC [SEQ ID NO: 11]
and
15.176B, 5'-CATTAACCGGTAAGCTTGGGGCTGGGG [SEQ ID NO: 12], and cloned into CN95. The virus created by homologous recombination of CN96 and BHG10 was designated CN706.

2. Attenuated Ad5 with PSE Driving Ad5 E1A Deleted for the Ad5 Endogenous Promoter and Enhancer.

In order to reduce ubiquitous expression of the E1A gene we decided to delete the endogenous E1A transcription regulatory DNA sequences. The transcriptional regulatory sequences of the E1A gene are intricately embedded in DNA sequences essential for DNA packaging (see Graeble and Hearing (1992) and References cited therein). Graeble and Hearing (1990) have shown that an Adenovirus 5 with a deletion from bp 194 to bp 316 which eliminates all transcriptional regulatory elements and retains only three out of seven packaging signals reduced the yield only 3-fold compared to wild type. These observations suggested that the E1A transcription regulatory sequences are dispensable and the loss of the first three out of seven packaging signals allowed virus production in acceptable quantities.

a. In the first variant, the region of the Ad5 genome containing the E1A enhancer and promoter and the Ad5 packaging sequence were deleted and replaced with a synthetic DNA segment containing a mutated packaging sequence and a PCR amplified segment of the PSE from CN127. In this construction the EcoRI/Xbal fragment of pXC.1 containing the first 1339 bases of the Ad5 genome was cloned into pUC19 to construct CN172 as a substrate for further manipulations. The DNA sequences corresponding to Ad5 nt 123 to nt 497 were deleted from CN172 by PCR amplification using primers:

26.153.1, 5'-CCGCTCGAGATCACACTCCGCCACAC [SEQ ID NO: 13], containing an XhoI site, and 26.153.2, 5'-CCGCTCGAGCACTCTTGAGTGCCA [SEQ ID NO: 14], containing an XhoI site. Cleavage of the PCR product with XhoI followed by religation resulted in CN178 in which an XhoI site replaced Ad5 nt 123 to 497. The synthetic DNA segment containing the mutated Ad5 packaging sequences was composed of the following two strands:

26.160.1: 5'-TCGAGGGATGTTGTAGTAAATTTGGGCGTAACCGAGTAAGATTTGGCCATTTTCGCGGGAAAACTGAATAAGACTCTTCGAAATCTGAATAATTTTGTGTTACTCATAGCGCGTAATATTTGTCTAGGGCCGCGGGGACTTTGACCGTTTACGTGG [SEQ ID NO: 15]

26.160.2: 5'-
GATCCCACGTAAACGGTCAAAGTCCCCGCGGCCCTAGACAAATATTACGCGCTATGAG
TAACACAAAATTATTCAGATTTCGAAGAGTCTTATTCAGTTTTCCCGCGAAAATGGCC
AAATCTTACTCGGTTACGCCCAAATTTACTACAACATCCC [SEQ ID NO: 16]

The strands were annealed and kinased using T4 polynucleotide kinase to form the dsDNA and allow ligation to the other DNA segments in the construct.

The PSE segment used for ligation was PCR amplified from CN127 using primers:

26.160.3, 5'-GGAAGATCTGAAATCTAGCTGATATAG [SEQ ID NO: 17], containing an XhoI site, and 19.16.5, 5'-TTCTCGAGAAGCTTGGGGCTGGGG [SEQ ID NO: 18], containing XhoI and HinDIII sites. For ligation, the PSE PCR product and CN178 were both cleaved with XhoI. The XhoI cut CN178, XhoI cut PSE PCR product, and the kinased packaging oligonucleotide were mixed in equal molar ratios and ligated with T4 DNA ligase. The resulting recombinant was designated CN201. The EcoRI/XbaI segment of CN201 containing the mutated packaging sequence and PSE driving E1A was excised from CN201 and used to replace the homologous segment of pXC.1 to generate CN202.

b. In the second variant, a different strategy was employed. In order to perform the deletion mutagenesis with a relatively small plasmid, a 2297 bp EcoRI-XhoI fragment of plasmid CN145, which contains the left end Adeno sequences including the E1A promoter region and the PSA enhancer, was subcloned into similarly cut pBluescript SKII+ yielding plasmid CN169.

The plan for the deletion mutagenesis was to delete the sequences from Ad position 194–301 and replace them with a SalI restriction site 5'-GTCGAC-3' which served as diagnostic marker to distinguish mutagenized plasmids from parental plasmids. The deletion eliminated all E1A core and E2F transcription regulatory elements as well as packaging signals AI and AII, but will preserve packaging signals AIII, AIV, AV, AVI and AVII. To this end, two oligonucleotide primers were synthesized:

28.134A, 5'-
GTCGACGTGAAATCTGAATAATTTTGTGTTACTCATAGC
[SEQ ID NO:19].

This primer matches to sequences 302–334 in Ad5.

28.134b,
5'-CACCGGCGCACACCAAAAACGTC [SEQ UD NO:20].

This primer matches to sequences 171–193 in Ad5.

The PCR mutagenesis kit from Stratagene was used in the following manipulations. In a PCR tube, 15 pMol of each primer was added to 0.5 pMol CN169; 1 mM dNTP, 2.5 μl 10× PCR 11 (Stratagene), dH$_2$O to 24 μl and 0.5 μl each of Taq Polymerase and TaqExtender (Stratagene). The mixture was overlaid with 20 μl mineral oil and programmed for PCR: 94° C. 4 minutes, 63° C. 1 minute, 72° C. 4 minutes for cycle and 94° C. 1 minute, 63° C. 1 minute, 72° C. 4 minutes for 10 cycles. 1 μl Dpn I restriction enzyme (Stratagene) was added to cut parental DNA and incubated at 37° C. for 80 minutes followed by the addition of 1 μl Pfu Polymerase (Stratagene) and incubation at 72° C. for 50 minutes to fill up protruding DNA ends generated during the former PCR process by the Taq polymerase. The PCR yielded a 5 kb linear DNA which was ligated with T4 DNA ligase to recircularize. XL-1 bacteria were transformed with the ligation reaction and mutagenized recombinants were identified by virtue of the presence of the unique SalI restriction site. One of the recombinants, CN 179, was used to rebuild the parental plasmid CN145 with the deletion by swapping the EcoRI-XhoI fragment of CN145 containing the Adeno-and PSE sequences with the one of CN179, yielding plasmid CN185. Plasmid CN185 was used in cotransfections with BHGll into human 293 cells to generate recombinant Adenoviruses. Nine virus plaques were isolated. One virus isolate was designated CN724.

3. Attenuated Ad5 with PSE Driving Expression of E1B.

The E1B protein functions in trans and is necessary for transport of late mRNA from the nucleus to the cytoplasm. Defects in E1B expression also results in poor expression of late viral proteins and an inability to shut off host-cell protein synthesis. The promoter of E1B has been implicated as the defining element of difference in the host range of Ad40 and Ad5: clinically Ad40 is an enterovirus, whereas Ad5 causes acute conjunctivitis (Bailey, Mackay et al. (1993) *Virology* 193: 631; Bailey et al. (1994) ibid 202: 695–706). The E1B promoter of Ad5 consists of a single high-affinity recognition site for Sp1 and a TATA box.

To insert a PSE driving expression of E1B in Ad5, an EagI site was created upstream of the E1B start site by inserting a G residue at Ad5 nt 1682 by oligonucleotide directed mutagenesis as above. To simplify insertion of the PSE in the EagI site the endogenous EagI site in CN95 was removed by digestion with EagI, treatment with mung bean nuclease, and relegation to construct CN114. The primers:

15.133a, 5'-TCGTCTTCAAGAATTCTCA [SEQ ID NO:21], containing an EcoRI site, and 9.4, 5'-GCCCACGGCCGCATTATATAC [SEQ ID NO:22], containing an extra C, were used to amplify the segment between the EcoRI site and Ad5 nt 1682.

Primers:

9.3, 5'-GTATATAATGCGGCCGTGGGC [SEQ ID NO:23]

containing an extra G, and 24.020, 5'-CCAGAAAATCCAGCAGGTACC [SEQ ID NO:23]

containing a KpnI site, were used to amplify the segment between 1682 and the KpnI site at Ad5 nt 2048. Co-amplification of the two segments with primers 9 and 12 yields a fragment with an EagI site at Ad5 nt 1682 which was used to replace the corresponding EcoRI/KpnI site in pXC.1 to construct CN124. PSE amplified from CN105 with primers:

26.1.1, 5'-TAACGGCCGTCTAGAAATCTAGCTGA [SEQ ID NO:25]
and
26.1.2, 5'-TAACGGCCGAAGCTTGGGCTGGG [SEQ ID NO:26], with EagI ends, was ligated into the EagI site of CN124 to construct CN125. The resultant virus from homologous recombination of CN125 and BHG10 was designated CN711.

4. Attenuated Ad5 with PSE Driving Expression of Both E1A and E1B.

A left end Ad5 plasmid with the PSE driving expression of both E1A and E1B was constructed by PCR amplifying CN95 with primers 9–12 as described for the construction of CN124. The resulting DNA segment contains the AgeI site derived from CN95 and the EagI site derived from the PCR mutagenesis. This DNA segment was cloned back into CN114 (the plasmid from which the EagI site was removed from pXC.1) to construct the plasmid CN144. CN144 contains a single AgeI site at Ad5 nt 547, and a single EagI site at Ad5 nt 1682. PSE segments were PCR amplified with AgeI ends from CN105 or EagI ends, also by PCR from CN105, as described above and ligated into the appropriate sites of CN144 to construct CN145. CN145 is a plasmid in which the PSE drives expression of both E1A and E1B while retaining the Ad5 endogenous promoters and enhancers of both genes. Clones with the PSE in the left to right orientation were chosen. The endogenous Ad5 E1A and E1B promoter/enhancers were moved upstream by insertion of both PSE segments. The resultant virus derived by homologous recombination of CN145 and BHG10 was designated CN716.

5. Attenuated Ad5 with PSE Driving Expression of E4.

E4 is located at the far right-hand end of the Ad5 genome and read right-to-left from the 1-strand (Flint, supra). E4 can be deleted from the Ad5 genome and supplied in trans by W162 cells, a derivative of VERO cells (Weinberg and Ketner, supra). The transcription products of E4 are complex. Open-reading frames (ORF) 3 and ORF 6 of the E4 transcription unit increase the accumulation of major late transcription unit mRNAs by binding the 55-kDa protein from E1B (Dix and Leppard (1993) *J. Virol.* 67: 3226–3231) and heterodimers of E2F-1 and DP-1 (Helin and Harlow (1994) *J. Virol.* 68: 5027–5035). Mutations such that neither ORF 3 nor ORF 6 encode functional proteins, produce plaques with an efficiency less than $10^{-6}$ that of wild-type virus (Bridge and Ketner (1989) *J. Virol.* 67: 5911–5921).

To facilitate insertion of the PSE driving E4 expression, the 10 kb EcoRI fragment of BHG10 containing the 3' 8 kb of Ad5 plus a portion of the pBR322 backbone was cloned into the EcoRI site of Bluescript KSII+ to construct CN108. A DraIII site at Ad nt 33906 was eliminated by partial digestion of CN108, endfilling with Klenow, and relegation to construct CN113. An XhoI site was introduced at Ad nt 35577 by oligonucleotide directed mutagenesis and linked PCR as described above using primers:

10.1, 5'-TAACTCACGTTGTGCATTGT [SEQ ID NO: 27], containing a DraII site, 10.4, 5'-GGTGCCGTGCTCGAGTGGTGT [SEQ ID NO: 28], containing an extra C, 10.3, 5'-ACACCACTCGAGCACGGCACC [SEQ ID NO: 29], containing an extra G, 19.158, 5'-GCTACTATTCGACAGTTTGTACTG [SEQ ID NO: 30], containing a ClaI site.

The PCR product containing an XhoI site as well as DraIII and ClaI ends was used to replace the corresponding DraIII/ClaI fragment of CN113 to construct CN122.

Plasmid CN70 contains the minimal PSE (from −5322 bp to −4023 bp relative to the transcription start site of the PSA gene) and −532 to +11 of the PSA promoter. CN70 was cut with XhoI/HindIII which removes the PSA promoter. A shorter promoter, from −230 to +7, amplified by PCR using primers:

18.119, 5'-GGACCTCGAGGTCTCCATGAGCTAC [SEQ ID NO: 31],
and
15.59B, 5'-AGCTCGAGCTTCGGGATCCTGAG [SEQ ID NO: 32], was ligated in it's place to construct CN104. CN127 was constructed from CN104 as follows: CN104 was cut with XhoI, endfilled with Klenow, and relegated to remove the XhoI site. The PSE from CN127 was PCR amplified using primers:

19.16.1, 5'-GGGTCGACGTACCTCTAGAAATCTAGC [SEQ ID NO: 33, and
19.16.5, 5'-TTGTCGACAAGCTTGGGGCTGGGG [SEQ ID NO: 34], to create SalI ends. This DNA segment was then ligated to XhoI cut CN122 to insert the PSE in the correct orientation upstream of E4. The resulting plasmid was designated CN135. The kanamycin resistance gene from pABS4 (Microbix) was inserted into CN135 at the PacI site to construct CN146; the EcoRI fragment of CN146 (containing the adenovirus sequences with the inserted PSE and kanamycin resistance gene) was then ligated to the large EcoRI fragment of BHG10, replacing the homologous wild type Ad sequences in BHG10. Recombinants were identified by resistance to both ampicillin and kanamycin, then the kanamycin gene was excised by PacI digestion and relegation to yield CN190 which is BHG10 with the PSE inserted upstream of the E4 coding region.

6. Attenuated Ad5 with PSE Driving Ad5 E1A containing Cytosine Deaminase in ΔE3.

A prostate specific adenovirus vector that contains the cytosine deaminase ("cd") gene incorporated into its genome could deliver this gene to targeted tissue (i.e. prostate tumors). Consequently, infected cancer cells would metabolize 5-FC and release the chemotherapeutic agent 5-FU into the surrounding tissue suppressing cell division, and exhibit the so-called "bystander effect" (Hirshowitz et al. (1995) *Human Gene Ther.* 6: 1055–1063; Griffith and Jarvis (1993) *J. Biol. Chem.* 268: 20085–20090). In contrast, noninfected, nonproximal cells would not be affected. This suggests two uses for the cd gene in an attenuated adenovirus vector. First, cd can serve as an additional therapeutic agent to provide a bystander killing ability and expedite local tumor reduction without systemic toxicity (Moolten and Wells (1990) *J. Nat'l Cancer Inst.* 82: 297–300).

Second, the gene can serve as a recall mechanism to halt a runaway infection by preventing viral DNA and RNA synthesis in infected and noninfected, local cells.

The enzyme cytosine deaminase, which deaminates cytosine to uracil, is found in many bacteria and fungi. These microorganisms can convert 5-fluorocytosine (5-FC), a harmless prodrug, to 5-fluorouracil (5-FU), a highly toxic compound that inhibits both DNA and RNA synthesis (Calibrisi and Chabner *Goodman and Gilman's The Pharmacological Basis of Therapeutics* (Eds. A. G. Gilman, T. Rall, A. S. Nies, and P. Taylor, Pergamon, N.Y.) (1990) 8 ed., pp 1209–1263); Damon et al. (1989). Because mammalian cells do not express significant amounts of the cd gene, they are not sensitive to 5-FU. Mammalian cells modified by gene transfer to express the gene can metabolize 5-FC, however. In this application, cd acts as a "suicide gene" selectively conferring sensitivity to those cells that contain the gene.

Adenovirus Vector Construction. The plasmid pCMV-cd, which contains cd coding region downstream of the CMV promoter, was obtained from David Crooks (Stanford). A SpeI restriction endonuclease site located in a multiple cloning region between the promoter and the cd ATG was removed by digesting the plasmid with enzymes which recognize sequences flanking the SpeI site, BamHI and EcoRI, filling the ends with klenow, and relegating (CN130). With this site removed, the CMV-cd cassette was cloned by digesting CN130 with SpeI and ligating the appropriate fragment into the XbaI site in pABS4 (Microbix, Toronto), a shuttle plasmid containing the kanamycin-resistance gene (CN131). By digesting CN131 with PacI, a fragment containing the KanR gene and the cd gene was isolated and ligated into similarly cut BHG11 (Microbix), which contains a unique PacI site engineered in the E3 region of Ad5 (CN141). The kanR gene was removed by digesting CN141 with SwaI and relegating the vector (CN148).

Two Ad5 recombinant viruses containing the cd gene in the E3 region were constructed. The first contains only the CMV-cd cassette in the E3 region (CN719). The second has the CMV-cd cassette in E3 and the prostate specific enhancer (PSE) minimal element modulating expression of E1A proteins (CN720). Viruses were generated by homologous recombination in low passage 293 cells, a human kidney cell line that expresses Ad E1A and E1B proteins, accomplished by cotransfecting them with pXC1/CN148 and CN145(PSE-E1A)/CN148.

In Vitro Characterization. In this first functional assay, CN720, an attenuated, prostate-specific adenovirus containing the cd gene in the E3 region, was studied to test its ability to confer 5-FC sensitivity on infected cells and neighboring cells. Wild type Ad5 (CN702) was also tested. CV1 cells, a semipermissive monkey kidney cell line, seeded in four, 96 well microtitre plates in DMEM, 5% PBS, were infected in a series of 1:2 dilutions from wells 1–11 with either CN702 or CN720. The multiplicity of infection of well one was approximately twenty-five for CN702 and two for CN720. Row 12 in each plate was left as an noninfected control. One day post infection the media was changed. Two plates of cells, one infected with CN720 and one infected with CN702, were treated with 5 mM 5-FC. The media on the remaining two plates was changed with complete DMEM only. These infected, untreated cells illustrate the lytic ability of the virus and were used to differentiate between the two causes of cell death in this experiment, virus cell lysis and 5-FU toxicity. The cells were fixed with 50% methanol-50% acetone and stained with Giemsa stain 6 days after the prodrug was administered. Plates were assayed by measuring absorbance at 530 nm in a SpectraMAX 340 microtitre plate reader (Molecular Devices). Cell survival was calculated by relating the absorbance of the cells in the noninfected wells to the absorbance in infected wells. The results were graphed as cell survival versus virus dilution.

Several conclusions can be made from this experiment. Most important, the graph suggests that the recombinant adenoviruses are expressing the cd gene. While the cell killing ability of both viruses appears to increase in the presence of 5-FC, perhaps due to a generalized toxicity to high concentrations of the prodrug, the change in cell killing is dramatic for CN720. The graph of CN720 shows a clear cell survival difference between 5-FC treated cells and untreated cells indicative of a 5-FU bystander effect. This result illustrates the potential to exploit cd function to either enhance the killing potential of Ad5 or to harness a runaway infection by generating an intracellular pool of toxic drug in noninfected cells that prevents DNA replication, a recall mechanism.

As an in vitro model, six 96 well plates were seeded with a human intestine epithelia cell line, DLD-1, that is permissive to human Ad in DMEM, 10% FBS. They were infected as described above with Ad5-cd virus (CN719). Prodrug (1 mM) was added to one plate at each time point, 0 hrs, 24 hrs, and 48 hrs post infection. The remaining three plates were untreated and served as infected controls. One set of two plates, one with prodrug, one without, was harvested on day 7, 8, and 9 post infection.

These results corroborate the previous data and extend it. Increased cell death is seen at all time points in infected pro-drug treated cells relative to infected but untreated cells. These data also reveal that the bystander effect is more pronounced as the infection becomes more advanced. When 5-FC is added at 24 hours and at 48 hours post infection, cell death is greater than when the prodrug is added immediately after initial infection. These data demonstrate that a tissue specific adenovirus harboring the cd gene has superior killing ability to wild type adenovirus.

7. Attenuated Ad5 with PSE Driving E1A and SV40 T Antigen in ΔE3 to Increase Host Range to Include Monkey and Human Cells Human adenovirus does not efficiently replicate in monkey cells. Associated with decreased levels of fiber mRNA in the cytoplasm, the abortive infection is caused by defects in the late gene expression regulated by E4 proteins (Ross and Ziff (1992) *J. Virology* 66: 3110–3117). Adenovirus-SV40 hybrids—shown to contain a small portion of the SV40 genome coding for the large T antigen integrated into the E3 region of the adenovirus 2 genome, overcome this defect and lyse monkey cells (Lewis and Rowe (1970) ibid 5: 413–420; Lewis et al, (1973) ibid 11: 655–664). The large T antigen (Tag) is believed to confer this host-range capability on these hybrids (Tijan et al., (1979) *PNAS* 75: 1279–1283). Several Ad2-SV40 hybrids have been isolated from SV40 and Ad2 infected cultures, each containing a conserved amount of the Tag carboxy terminal coding region and varying lengths of amino terminal coding region.

We have adopted this paradigm to develop Ad5 tissue specific, host-range mutants for use in monkey studies. Two strategies were undertaken. The first used the host-range mutant Ad2+ND1, which harbors SV40 Tag coding sequence from map units 0.28–0.11, as a model (Zain & Roberts (1978) *J. Mol. Biol.* 120: 13). A 666 base pair PstI/BamHI restriction fragment in the plasmid pDIS (obtained from Edgar Schrieber), a plasmid which contains the entire Tag coding sequence, the endogenous SV40 early promoter, and an inverted SV40 enhancer, contains the appropriate 3' sequence and was cloned via the shuttle plasmid pABS4 (Microbix) into the unique PacI restriction site in the E3 region of BHG11 (Microbix). Upstream of the coding sequence was cloned an oligo (+) strand:

26.99.1, 5'GTTTGTGTATTTTAGATCAAAGATGCTGCA [SEQ ID NO: 35], and (−) strand:

26.99.2, 5'-GCATCTTTGATCTAAAATACACAAAC [SEQ ID NO: 36], that contains a splicing acceptor sequence, ribosome recognition sequences, and an ATG to achieve expression of the appropriate peptide (CN170). Expression of this construct is dependent on a transcript originating from the major late promoter.

The second strategy involved creating an internal deletion in the Tag sequence in the plasmid pDIS between the EcoNI site in the amino terminal region and the PstI site in the carboxy terminal coding sequence by using an adapter oligo (+) strand:

27.183.1, 5'-TAAAGGAGGAGATCTGCCTAAAACACTGCA [SEQ ID NO: 37], and (−) strand:

27.183.2, 5'-GTGTTTTAGGCAGATCTCCTCCTTT [SEQ ID NO: 38].

The entire transcription unit, including the enhancer, promoter, and the coding sequence was excised by HpaII/BamHI digestion and cloned via shuttle plasmid into the unique PacI site of BHG11 (CN183). This method generates a discrete transcription unit in Ad5 sequence whose expression is not dependent on the major late promoter.

Two host-range Ad5-SV40 viruses were produced. Both contain the carboxy termini of the Tag but lack the promoter. One is a tissue-specific, attenuated virus with the prostate specific enhancer (PSE) modulating expression of the E1A proteins (CN725). The other is wild type Ad5 with a Tag insertion (CN726). Both were generated by homologous recombination by cotransfecting 293 cells, a human kidney cell line that expresses Ad E1A and E1B proteins, with CN145(PSE-E1A) or pXC1 (wild type Ad5 left hand end) and CN170.

Host-Range Mutant Characterization. Wild type Ad5 (CN702) and CN726 were plaqued on both 293 cells and CV1 cells, an African Green Monkey kidney cell line. Plaques were counted in both cell monolayers and a ratio between the plaques in the two cell lines was determined. The ratio for CN726 and CN702 was 0.01 and 0.0007, respectively. The capability of replication of adenovirus in monkey cells allows preclinical evaluation of recombinant attenuated adenoviruses in monkeys, yielding valuable information for dosage and formulation of these viruses as therapeutic agents in humans.

8. Construction of Recombinant DNA to Introduce Mutations in E2, the DNA Binding Protein (DBP), for the generation of Recombinant Ad5 with Extended Host Range Allowing Replication in Human and Monkey Cells.

Wild type adenovirus type 5 is only replication competent in human cells. For preclinical evaluation of therapeutic attenuated adenoviruses it would be desirable to test efficacy and toxicity in large human-like animals such as monkeys. A host range mutant hr404 has been described that confers a replication phenotype of human Ad5 in monkey cells (Klessig & Grodzicker (1979) Cell 17: 957–966). The nature of the hr404 mutation was shown to be a single point mutation C→T at adeno position 32657 in the DBP gene resulting in a change of Histidine to Tyrosine amino acid at codon 130 (H1130Y) in the 72K DNA binding protein (Kruijer et al. (1981) Nucleic Acids Res. 9: 4439–4457).

We constructed a recombinant DNA molecule with the 5.8 kb EcoRI-BamHI fragment from plasmid BHG 10 (Bett et al., supra) containing the right end sequences of Adenovirus type 5 and introduced by site-directed mutagenesis the H130Y mutation in the DBP gene. This plasmid should allow the construction of recombinant adenoviruses which are capable to replicate in human and monkey cells.

The 5769 bp EcoRI-BamHI fragment of BHG10 (Bett et al., supra) was cloned into similarly cut pBluescript KSII+ resulting in plasmid CN184. In order to eliminate disturbing restriction sites, a 2568 bp XhoI fragment was deleted yielding plasmid CN 186. The mutagenesis upper PCR primer reads:

28.180U, 5'-GCAACCCACCGGTGCTAATCAAGTATGGCAAAGGAGTAAGCGC-3' [SEQ ID NO: 39]

The mutated T residue causing the H130Y mutation is shown in bold underlined style. Shown in italics is the unique SgrAI site in pCN186. The lower PCR primer reads:

28.180L, 5'-TGGCCTTGCTAGACTGCTCCTTCAGC-3' [SEQ ID NO: 40]

PCR amplification was done with 100 pMol of each of these primers, 200 ng CN186 as template, 1 mM dNTP, 1× Pfu buffer (Stratagene), dH$_2$O to 100 μl, and 5U cloned Pfu polymerase (Stratagene) at 94° C. 1 minute, 60° C. 1 minute, 72° C. 2 minutes for 30 cycles. The PCR yielded the expected DNA fragment of 588 bp. The DNA fragment was purified with a Wizard DNA clean-up column (Promega) and digested with restriction enzymes SgrAI and AflII. The 473 bp fragment of interest containing the H130Y mutation was gel purified and isolated. For reinsertion into the DBP gene, the mutated DNA fragment was ligated with the 1639 bp AscI-SgrAI fragment from CN184 and the 6609 bp AflII-AscI fragment from CN184 resulting in plasmid CN188.

Recombinant adenovirus genomes were constructed by in vitro ligation of the 5.8 kb EcoRI-BamHI fragment of CN188 with a 21562 bp EcoRI-Bst1107 center DNA fragment of BHG10 and Bst1107-cut plasmid CN144. The resultant virus was designated CN723.

The capability of replication of adenovirus in monkey cells allows preclinical evaluation of recombinant attenuated adenoviruses in monkeys, yielding valuable information for dosage and formulation of these viruses as therapeutic agents in humans. Further, with the use of the hr404 mutation in CN723, the same virus used for monkey studies can be used as the human clinical trial virus.

9. Deletion of ORF 1,2,3 and part of ORF 4 from the E4 Region of Adenovirus Type 5.

The E4 region codes for two polypeptides which are responsible for stimulating the replication of viral genomic DNA and for stimulating late gene expression. The protein products of open reading frames (ORFS) 3 and 6 can both perform these functions, however the ORF 6 protein requires interaction with the E1B 55K protein for activity while the ORF 3 protein does not. To further restrict viral replication to prostate epithelial cells E4 orfs 1–3 can be deleted, making viral DNA replication and late gene synthesis dependent on E4 ORF 6 protein. By combining such a mutant with sequences in which the E1B region is regulated by the PSE, a virus can be obtained in which both the E1B function and E4 function are dependent on the PSE driving E1B.

A virus of this type was constructed by combining sequences from the plasmid dl1006 which contains an E4 deletion of ORFS 1–3 (Bridge & Ketner, J. Virol. (1989) 63: 631–638) with BHG10, followed by co-transfection with CN144 to construct a recombinant virus. The plasmid pd11006 is cleaved with AvrII and AgeI to isolate sequences containing the mutated E4 region. This DNA segment is used to replace the homologous segment of CN108 cleaved with the same enzymes.

CN108 contains the 6kb EcoRI fragment from BHG10 cloned into BSKSII+. Due to the E3 deletion in BHG10, the AvrII site at Ad5 nt 28752 had been deleted. AvrII still cut CN108 at Ad5 nt 35463; AgeI cut CN108 at Ad5 nt 31102. The 4.4 kb AvrII/AgeI fragment from CN108 was replaced with the 3.8 kb AvrII/AgeI fragment from dl1006 producing CN203 containing the E4 deletion. The EcoRI fragment from CN203 was cloned into BHG10 to construct CN204. Homologous recombination of CN204 and CN144 yielded the virus CN726.

A similar virus of this type was constructed in the following manner. As previously described AvrII cut CN108 at Ad5 nt 35463. SapI cut CN108 twice, with one of the sites at Ad5 nt 34319. A complete AvrII cut and a partial SapI cut of CN108 and religation removed 1144 bp from E4 yielded CN205. The 5.3 kb EcoRI/BamHI fragment from CN205 was cloned into similarly cut CN188 yielding CN206. The 14 kb BamHI fragment of CN206 containing both the E4 deletion and the hr404 mutation was cloned in BamHI cut BHG10 producing CN207. Homologous recombination of CN144 and CN207 in 293 cells yielded CN727.

10. PSE Controlling the E2 Region of Ad5

The E2 region of Adenovirus 5 codes for proteins related to replication of the adenoviral genome, including the 72 kDa DNA-binding protein, the 80 kDa precursor terminal protein and the viral DNA polymerase. The objective is to control expression of the E2 genes by the prostate-specific PSA enhancer/promoter in a recombinant adenovirus.

The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1a transactivator protein, the E2 early promoter is crucial during the early phases of viral replication.

The E2 early promoter, mapping in Ad5 from nt 27053–27121 consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan & Thimmapaya, Current Topics in Microbiology and Immunology (1995) 199 part 3: 177–194.

The E2 late promoter overlaps with the coding sequences of the L4 gene encoded by the counterstrand and is therefore not amenable for genetic manipulation. However, the E2 early promoter overlaps only for a few base pairs with sequences coding for a 33 k protein on the counterstrand. Notably, the SpeI restriction site (Ad5 position 27082) is part of the stop codon for the above mentioned 33 kDa protein and conveniently separates the major E2 early transcription initiation site and TATA-binding protein site from the upstream transcription factor biding sites E2F and ATF. Therefore, an insertion of the PSA enhancer/promoter into the SpeI site would disrupt the endogenous E2 early promoter of Ad5 and should allow prostate-restricted expression of E2 transcripts.

Construction of recombinant Ad5 with the PSA enhancer/promoter in the E2 early promoter region. The BamHI-EcoRI fragment of Ad5 (positions 21562–27331) encompassing the E2 region was previously subcloned into pBluescript KSII+ resulting in plasmid CN184. A variant of this plasmid, CN188, carrying a mutation in the DBP gene (H130Y) allowing extended host range applications has been constructed and described above.

Plasmid CN188 was used for insertion of the PSA enhancer/promoter into the E2 region. The plasmid was linearized with SpeI and the 5' protruding ends were dephosphorylated with calf intestine alkaline phosphatase and then end-filled with Klenow polymerase and dNTP. The blunt ended PSE enhancer/promoter was ligated to SpeI linearized, blunt ended vector CN188. Recombinant DNAs with the PSE enhancer/promoter in the appropriate orientation for directing transcription initiation into the E2 region were identified. Plasmid CN196 contains the PSE enhancer/promoter in the backbone of CN188. The 5.3 kb EcoRI fragment of plasmid CN205, containing a deletion of the orf 1, 2, 3 and 4 of the E4 gene, was inserted in the appropriate orientation into EcoRI cut CN196, yielding plasmid CN197.

A recombinant viral genome with the PSE enhancer/promoter controlling expression of the E1A, E1B and the E2 early genes and the hr404 mutation H130Y in the DBP gene and deletion of open reading frames 1, 2, 3, and 4 of the E4 gene was obtained by in vitro ligation of the 9152 bp BamHI-Bst11071 fragment of CN144 with the 15802 bp Bst11071-BamHI fragment of BHG10 and the 12425 bp BamHI fragment of CN197.

Virus Preparation

Viruses were prepared as described previously (above). The table below lists the combinations of right end and left end Ad5 plasmids used to generate recombinant Ad5 with the desired features:

| Virus | Name | Left End Plasmid | Right End Plasmid |
| --- | --- | --- | --- |
| PSE-E1A | CN704–708 | CN96 | BHG10 |
| PSE-E1A | CN718 | CN145 | BHG10 |
| PSE-E1B | CN711 | CN125 | BHG11 |
| PSE-E1A/E1B | CN716 | CN144 | BHG10 |
| PSE-E1A/E1B | CN717 | CN144 | BHG10 |
| PSE-E4 | | pXC.1 | CN135-BHG10 |
| ΔEnh/PSE-E1A | CN724 | | BHG10 |
| PSE-E1A, ΔE3 CMV-SV40 T Ag | CN725 | CN96 | CN183 |

-continued

| Virus | Name | Left End Plasmid | Right End Plasmid |
|---|---|---|---|
| PSE-E1A/E1B, with HR404 with ΔE3 CMV-CD | CN723 | CN144 | CN188, CN108, BHG10 |
| PSE-E1A/E1B, ΔE4 (dl1006) | CN726 | CN144 | CN207 |
| PSE-E1A/E1B, hr404, ΔEA | CN727 | CN144 | CN207 |

Results:
Virus construction and genomic structure.

In the initial round of construction three replication competent, prostate-specific adenoviruses were produced. CN706 which contains the PSE driving the expression of the E1A gene, CN711 which contains the PSE driving the expression of the E1B gene, and CN716 which contains the PSE driving E1A expression and the PSE driving E1B expression. The viruses were generated by homologous recombination in 293 cells and cloned twice by plaque purification. The structure of the genomic DNA was analyzed by PCR and sequencing of the junctions between the inserted sequences and the Ad genomic sequences. All viruses contained the desired structures (data not shown).

Virus growth in vitro.

The growth of the viruses in vitro was characterized by two assays: a burst size assay to measure the amount of infectious particles produced in one round of infection and plaque assays to assess the growth of the viruses in various types of cells.

For the burst size assays either LNCaP cells (a CaP cell line which produces PSA) or HBL100 cells (a non-malignant breast epithelial cell line) were infected with virus at a multiplicity of infection (MOI) of 1 ($5 \times 10^5$ PFU per sample). At various time points samples were harvested and the amount of infectious virus present measured by plaque assays on 293 cells. Table 2 shows that CN706 produced $6.3 \times 10^6$ pfU from an input of $5 \times 10^5$ pfu in LNCaP cells after 48 hours. In HBL100 cells the increase from the same amount of input virus was to $2.0 \times 10^6$ pfu. CN706 then yielded 13 pfu per input infectious particle in LNCaP cells which was 3 fold greater than that produced in HBL100 cells over the same time period.

Burst size assays on CN711 also revealed preferential growth in LNCaP cells versus HBL100 cells (Table 2). In LNCaP cells $5 \times 10^5$ pfu input virus produced $4 \times 10^7$ pfu at 48 hours while in HBL100 cells $8 \times 10^6$ pfu were obtained at 48 hours. This represented a 40 fold increase in virus in LNCaP cells or a 5 fold greater yield than in HBL100 cells.

The differential in virus production for CN716 showed a wider disparity between the two cell lines. In LNCaP cells $1.7 \times 10^7$ pfu were obtained after 48 hours while in HBL100 cells $8 \times 10^5$ pfu were obtained at the same time point. Therefore in LNCaP cells 34 infectious particles were produced for each input particle at 48 hours while for HBL100 1.6 infectious particles was produced.

These results indicate that the expression of the early genes E1A and E1B can be controlled by the inserted PSE. To further characterize this regulation, production of CN706 virus was assayed by the burst assay in LNCaP cells in the presence or absence of the testosterone analog R1881. Since the PSE is highly active in the presence of androgens but essentially inactive in the absence of androgens, the production of early proteins controlled by the PSE and therefore the production of virus should be sensitive to androgen levels. As shown in Table 3 in the absence of R1881, $3 \times 10^6$ pfu were obtained at 48 hours for a three fold increase over input virus. In the presence of 1 nM or 10 nM R1881 two to three fold more pfu were obtained at 48 hours. In contrast, with wild type adenovirus assayed in parallel, no difference was evident in pfu obtained in the presence or absence of R1881.

TABLE 2

Burst Assays

| | LNCaP | HBL100 |
|---|---|---|
| CN706 | $6.3 \times 10^6$ | $2.0 \times 10^6$ |
| CN711 | $4 \times 10^7$ | $8 \times 10^6$ |
| CN716 | $1.7 \times 10^7$ | $8 \times 10^5$ |

TABLE 3

R1881 induction

| | 0 nM R1881 | 1 nM R1881 | 10 nM R1881 |
|---|---|---|---|
| CN706 | $3 \times 10^6$ | $8 \times 10^6$ | $5 \times 10^6$ |

To further assess the growth selectivity of CN706, CN711, and CN716, the viruses were analyzed in plaque assays in which a single infectious viral particle produces a visible plaque by multiple rounds of infection and replication. The results of a representative assay are shown in Table 4.

TABLE 4

Plaque assay
Cell line

| | 293 | LNCaP | HBL100 | TSU | A549 |
|---|---|---|---|---|---|
| CN702 | $2.3 \times 10^5$ | $4.1 \times 10^5$ | $4.3 \times 10^5$ | $1.1 \times 10^6$ | $5.1 \times 10^5$ |
| CN706 | $2.3 \times 10^5$ | $4.4 \times 10^4$ | $1.7 \times 10^3$ | $5.4 \times 10^4$ | $2.9 \times 10^4$ |
| CN711 | $2.3 \times 10^5$ | $5.5 \times 10^5$ | $2.7 \times 10^5$ | $1.6 \times 10^5$ | $2.6 \times 10^5$ |
| CN716 | $2.3 \times 10^5$ | $6.9 \times 10^5$ | $2.7 \times 10^3$ | $4.4 \times 10^3$ | $4.1 \times 10^4$ |

Virus stocks were diluted to equal pfu/ml, then used to infect monolayers of cells for 1 hour. The inoculum was then removed and the cells were overlayed with semisolid agar containing medium and incubated at 37° C. for one week. Plaques in the monolayer were then counted and titers of infectious virus on the various cells were calculated. The data were normalized to the titer of CN702 on 293 cells.

The wild type virus CN702 showed approximately equal titers on each of the five cell lines. In contrast, each of the PSE modified viruses displayed a variable pattern of growth on the different cell types. CN706 grew to a 10 fold lower titer on LNCaP cells as on 293 cells, however, its titer on HBL100 cells was 260 fold lower than on 293 cells. On the Non-PSA secreting CaP cell line TSU the titer of CN706 was approximately the same as on LNCaP cells which do secrete PSA. Similarly, the titer on the lung cell line A549 was also close to that on LNCaP cells. The virus CN711 displayed no significant difference in titer on the cell lines tested.

The data for the CN716 virus revealed a marked selectivity for growth in the LNCaP cell line. This virus grew well in LNCaP cells, reaching an even higher titer than on 293 cells. Growth of the virus on other cell lines was significantly lower, 18 fold lower on the next highest titer line, A549. The greatest differential was on HBL100 cells, where the titer was 225 fold lower relative to that on LNCaP cells. The data from the burst size assay and the plaque assay demonstrate that human adenovirus can be modified using the PSE to develop viruses with selective growth properties for PSA secreting CaP cells.

Treatment of LNCaP tumor xenografts.

The ultimate objective in the development of prostate-specific viruses is to treat patients with prostate disease. The feasibility of this objective was tested using LNCaP tumor xenografts grown subcutaneously in Balb/c nu/nu mice. The test viruses were inoculated into the mice either by direct intratumoral injection of approximately $10^8$ pfu of virus in 0.1 ml PBS+10% glycerol or intravenously via the tail vein. Tumor sizes were measured and, in some experiments, blood samples were taken weekly.

The effect of intratumoral injection of CN706 on tumor size and serum PSA levels was compared to sham treatment. The sizes of the CN706 treated tumors continued to increase for two weeks, then progressively decreased for the duration of the experiment. At the end of the experiment all of the CN706 treated tumors (10 total) had diminished in size and five mice were cured of their tumor. In contrast, the buffer treated tumors continued to grow for the duration of the experiment, reaching approximately twice their original size by 42 days.

Previously published results have shown that serum PSA levels correlate with tumor size in the LNCaP tumor xenograft model. Measurement of PSA levels in the mice with tumors treated with CN706 indicated a rise in PSA levels one week after treatment, followed by a steady decline in PSA levels out to 35 days. Serum PSA levels increased during the course of the experiment, averaging over 250 ng/ml at 35 days.

While it is likely that a therapeutic based on the viruses described here would be given intralesionally, it would also be desirable to determine if the virus can affect tumor growth following intravenous administration. If so, then it is conceivable that the virus could be used to treat metastatic tumor deposits inaccessible to direct injection. Groups of five mice bearing LNCaP tumors were inoculated with $10^8$ pfu of CN706 by tail vein injection, or $10^8$ pfu of a replication defective adenovirus (CMV-LacZ) to control for non-specific toxic effects of the virus, or with buffer used to carry the virus. Tumors in mice treated with buffer or CMV-LacZ continued to grow for the duration of the experiment, ultimately reaching approximately five times their original size on average. Tumors in mice treated with CN706 grew slightly between the time of inoculation and the first measurement at 7 days, then the average tumor size diminished to approximately 75% of the original tumor volume by day 42.

Treatment of LNCaP tumors in nude mice with CN711 resulted in a similar outcome to treatment with CN706. In the CN711 treated animals (5 total) the tumors continued to grow between inoculation and day 8. Thereafter the average tumor size diminished, reaching 65% by day 49. The average tumor size of the buffer treated mice (4 total) increased through the duration of the experiment, reaching 300% of the original tumor volume by 49 days.

The same experimental protocol was used to test the CN716 virus in LNCaP tumors. Mice were inoculated with PBS+10% glycerol, CN716, or CN702. The tumors in the buffer mice grew rapidly and the mice were sacrificed due to large tumor sizes after three weeks. Tumors treated with CN702 continued to grow for two weeks, then diminished in size to 80% of their original volume by day 42. Tumors treated with CN716 remained at their original size for one week, then diminished in size to 40% of their original size by day 42. At the end of the experiment 2 of the 4 mice treated were cured of their tumors.

It is evident from the above results that adenoviruses can be provided as vehicles specific for particular host cells, where the viruses may be replication defective or replication competent. The viruses may be vehicles for a wide variety of genes for introduction in the target host cells. Particularly, employing the prostate specific element, the early genes essential for replication may be modified so as to be under the control of prostate cell responsive elements.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An adenovirus vector comprising an adenovirus gene essential for propagation under transcriptional control of a prostate specific response element, said prostate cell specific response element comprising an enhancer specific for prostate specific antigen and a promoter.

2. An adenovirus vector according to claim 1, wherein said adenovirus gene is an early gene.

3. An adenovirus vector according to claim 1, further comprising a transgene, wherein the transgene is under transcriptional control of a prostate specific response element, wherein the prostate specific response element comprises an enhancer specific for transcription of prostate specific antigen and a promoter.

4. An adenovirus vector according to claim 3, wherein the transgene is cytotoxic.

5. An adenovirus vector according to claim 1, wherein the prostate specific response element comprises a prostate specific antigen enhancer.

6. An adenovirus vector according to claim 5, wherein the prostate specific antigen enhancer comprises nucleotides –5322 and –3739 relative to the transcription start site of prostate specific antigen gene.

7. An adenovirus vector according to claim 6, wherein said adenovirus gene is an early gene.

8. An adenovirus vector according to claim 1, wherein the promoter is from a prostate cell specific protein gene.

9. An adenovirus vector according to claim 8, wherein the promoter is from a prostate specific antigen gene.

10. An adenovirus vector according to claim 9, wherein the promoter is nucleotides –540 to +8 relative to transcription start site of prostate specific antigen gene.

11. An adenovirus vector according to claim 1, wherein said adenovirus vector has a deletion in at least one region between adenovirus nucleotides 300 to 3600 and 27000 to 31000.

12. An in vitro cell transformed with an adenovirus vector of claim 1.

13. An in vitro cell transformed with an adenovirus vector of claim 3.

14. An in vitro cell transformed with an adenovirus vector of claim 5.

15. A composition comprising an adenovirus vector of claim 1.

16. A composition comprising an adenovirus vector of claim 3.

17. A composition comprising an adenovirus vector of claim 5.

18. A composition of claim 15, further comprising a physiologically acceptable carrier.

19. A composition of claim 16, further comprising a physiologically acceptable carrier.

20. A composition of claim 17, further comprising a physiologically acceptable carrier.

21. A method for propagating an adenovirus specific for mammalian cells expressing a prostate specific protein, said method comprising combining an adenovirus vector of claim 1 with mammalian cells expressing a prostate specific protein, whereby said adenovirus is propagated.

22. A method for propagating an adenovirus specific for mammalian cells expressing a prostate specific protein, said method comprising combining an adenovirus vector of claim 3 with mammalian cells expressing a prostate specific protein, whereby said adenovirus is propagated.

23. A method for propagating an adenovirus specific for mammalian cells expressing a prostate specific protein, said method comprising combining an adenovirus vector of claim 5 with mammalian cells expressing a prostate specific protein, whereby said adenovirus is propagated.

24. An in vitro method for preparing an adenovirus vector of claim 1, comprising (a) co-transfecting two plasmids into a suitable cell, wherein one of said two plasmids comprises a left hand region of adenovirus and another of said two plasmids comprises a right hand region of adenovirus, and wherein one of the two plasmids comprises an adenovirus gene essential for propagation under the transcriptional control of a prostate specific response element for transcription of a prostate cell specific protein, said prostate specific response element comprising an enhancer specific for said prostate cell and a promoter; and (b) isolating the resultant adenovirus vector.

25. An in vitro method for preparing an adenovirus vector of claim 3, comprising (a) co-transfecting two plasmids into a suitable cell, wherein one of said two plasmids comprises a left hand region of adenovirus and another of said two plasmids comprises a right hand region of adenovirus, and wherein one of the two plasmids comprises an adenovirus gene essential for propagation under the transcriptional control of a prostate specific response element for transcription of a prostate cell specific protein, said prostate specific response element comprising an enhancer specific for said prostate cell and a promoter; and (b) isolating the resultant adenovirus vector.

26. An in vitro method for preparing an adenovirus vector of claim 5, comprising (a) co-transfecting two plasmids into a suitable cell, wherein one of said two plasmids comprises a left hand region of adenovirus and another of said two plasmids comprises a right hand region of adenovirus, and wherein one of the two plasmids comprises an adenovirus gene essential for propagation under the transcriptional control of a prostate specific response element for transcription of a prostate cell specific protein, said prostate specific response element comprising prostate specific antigen enhancer and a promoter; and (b) isolating the resultant adenovirus vector.

27. An in vitro method for using the adenovirus vector of claim 1, comprising introducing the adenovirus vector of claim 23 into a tumor cell expressing prostate specific antigen (PSA), wherein introduction of the adenovirus vector results in cytotoxicity.

28. An in vitro method for using the adenovirus vector of claim 3, comprising introducing the adenovirus vector of claim 3 into a tumor cell expressing prostate specific antigen (PSA), wherein introduction of the adenovirus vector results in cytotoxicity.

29. An in vitro method for using the adenovirus vector of claim 5, comprising introducing the adenovirus vector of claim 5 into a tumor cell expressing prostate specific antigen (PSA), wherein introduction of the adenovirus vector results in cytotoxicity.

30. A method for suppressing tumor growth comprising introducing the adenovirus vector of claim 1 into a tumor cell expressing prostate specific antigen (PSA), wherein introduction of the adenovirus vector results in suppression of tumor growth.

31. A method for suppressing tumor growth comprising introducing the adenovirus vector of claim 3 into a tumor cell expressing prostate specific antigen (PSA), wherein introduction of the adenovirus vector results in suppression of tumor growth.

32. A method for suppressing tumor growth comprising introducing the adenovirus vector of claim 5 into a tumor cell expressing prostate specific antigen (PSA), wherein introduction of the adenovirus vector results in suppression of tumor growth.

* * * * *

UNITED STATES PATENT AND TRADEMARK OFFICE

CERTIFICATE OF CORRECTION

PATENT NO. : 5,871,726            Page 1 of 3

DATED       : February 16, 1999

INVENTOR(S) : Daniel Robert Henderson and Eric Rodolph Schuur

It is certified that error appears in the above-identified patent and that said Letters Patent is hereby corrected as shown below:

Title page, in title, please delete "SUPPERSSION" and insert --SUPPRESSION--;

Title page, first column, under OTHER PUBLICATIONS, (Bridge et al. reference), before "Redundant" and after "4", please insert --"--;

Title page, first column, under OTHER PUBLICATIONS, (Calabresi et al. reference), please delete "Basos" and insert --Basis--;

Title page, second column, under OTHER PUBLICATIONS, (Grand et al. reference), please delete "Bio chem." and insert --Biochem.--;

Title page, second column, under OTHER PUBLICATION, (Helin et al. reference), before "Heterodimerization" and after "protein", please insert --"--;

Page 2, first column, under OTHER PUBLICATIONS, (Rosenfeld et al. reference), after "252", please delete ";" and insert --:--;

Page 2, first column, under OTHER PUBLICATIONS, (Tijan et al. reference), please delete "Tijan" and insert --Tjian--;

Page 2, second column, under OTHER PUBLICATIONS, please delete "Ko, A.S.C., et al., "Gene Therapy for the Treatment of Androgen Indpedent and Prostate Specific Antigen Producing Human Prostate Cancer," J. Cell. Biochem., Supp. 0, (21A):423 (1995).";

Page 2, second column, under OTHER PUBLICATIONS, please delete "Marshal. Science 269:1050-1055, Aug. 1995.";

Page 2, second column, under OTHER PUBLICATIONS, please delete "Culver et al. Trends in Genetics 10(5):174-178, May 1994.";

UNITED STATES PATENT AND TRADEMARK OFFICE
CERTIFICATE OF CORRECTION

PATENT NO. : 5,871,726
DATED : Feb. 16, 1999
INVENTOR(S) : Daniel Robert Henderson, et al It is certified that error appears in the above-indentified patent and that said Letters Patent is hereby corrected as shown below:

Page 2, second column, under OTHER PUBLICATIONS, please delete "Hodgson. Exp. Opin. Ther. Patents 5(5):459-468, 1995.";

Page 2, second column, under OTHER PUBLICATIONS, please delete "Miller et al. FASEB 9:190-199, Feb. 1995.";

Page 2, second column, under OTHER PUBLICATIONS, please delete "Gotoh et al., J. Urology 153, 4 Supp., 308A, Apr. 1995.";

Page 2, second column, under OTHER PUBLICATIONS, please delete "Taneja et al., Proc. Amer. Assoc. Canc. Res.,35(0):375, Mar. 1994.";

Column 5, line 60, please delete "selecting" and insert --selectins--;
Column 7, line 16, please delete ")";
Column 11, line 28, before "Toronto" please insert --(--;
Column 14, line 59, please delete "NO:23, and insert --NO:24--;
Column 18, line 53, please delete "Tijan" and insert --Tjian--;
Column 23, line 35, please delete "PFU"and insert --pfu--;
Column 23, line 39, please delete "pfU" and insert --pfu--;
Column 24, TABLE 2, line 12, please delete "6.3 x $10_6$" and insert --6.3 x $10^6$--;
Column 24, TABLE 2, line 13, please delete "4 x $10_7$" and insert --4 x $10^7$--;
Column 24, TABLE 2, line 14, please delete "1.7 x $10_7$" and insert --1.7 x $10^7$--;
Column 24, TABLE 3, line 23, please delete "3 x $10_6$" and insert --3 x $10^6$--;
Column 24, TABLE 3, line 23, please delete "8 x $10_6$" and insert --8 x $10^6$--;
Column 24, TABLE 3, line 23, please delete "5 x $10_6$" and insert --5 x $10^6$--;
Column 24, TABLE 4, line 37, please delete "2.3 x $10_5$" and insert --2.3 x $10^5$--;
Column 24, TABLE 4, line 37, please delete "4.1 x $10_5$" and insert --4.1 x $10^5$--;
Column 24, TABLE 4, line 37, please delete "4.3 x $10_5$" and insert --4.3 x $10^5$--;
Column 24, TABLE 4, line 37, please delete "1.1 x $10_6$" and insert --1.1 x $10^6$--;
Column 24, TABLE 4, line 38, please delete "2.3 x $10_5$" and insert --2.3 x $10^5$--;
Column 24, TABLE 4, line 38, please delete "4.4 x $10_4$" and insert --4.4 x $10^4$--;
Column 24, TABLE 4, line 38, please delete "1.7 x $10_3$" and insert --1.7 x $10^3$--;
Column 24, TABLE 4, line 38, please delete "5.4 x $10_4$" and insert --5.4 x $10^4$--;

UNITED STATES PATENT AND TRADEMARK OFFICE
CERTIFICATE OF CORRECTION

PATENT NO. : 5,871,726
DATED : Feb. 16, 1999
INVENTOR(S) : Daniel Robert Henderson, et al It is certified that error appears in the above-indentified patent and that said Letters Patent is hereby corrected as shown below:

Column 24, TABLE 4, line 39, please delete "2.3 x 10$_5$" and insert --2.3 x $10^5$--;
Column 24, TABLE 4, line 39, please delete "5.5 x 10$_5$" and insert --5.5 x $10^5$--;
Column 24, TABLE 4, line 39, please delete "2.7 x 10$_5$" and insert --2.7 x $10^5$--;
Column 24, TABLE 4, line 39, please delete "1.6 x 10$_5$" and insert --1.6 x $10^5$--;
Column 24, TABLE 4, line 40, please delete "2.3 x 10$_5$" and insert --2.3 x $10^5$--;
Column 24, TABLE 4, line 40, please delete "6.9 x 10$_5$" and insert --6.9 x $10^5$--;
Column 24, TABLE 4, line 40, please delete "2.7 x 10$_3$" and insert --2.7 x $10^3$--;
Column 24, TABLE 4, line 40, please delete "4.4 x 10$_3$" and insert --4.4 x $10^3$--;
Column 24, TABLE 4, line 40, please delete "4.1 x 10$_4$" and insert --4.1 x $10^4$--;
Column 43, claim 7, line 8, please delete "6" and insert --5--; and
Column 44, claim 27, line 32, please delete "23" and insert --1--.

Signed and Sealed this

Second Day of November, 1999

Attest:

Attesting Officer

Q. TODD DICKINSON

Acting Commissioner of Patents and Trademarks